United States Patent
Lin Lee et al.

(10) Patent No.: US 8,088,110 B2
(45) Date of Patent: Jan. 3, 2012

(54) AUTOMATICALLY RETRACTABLE SAFETY INJECTOR FOR NON-LIQUID MATERIAL

(75) Inventors: Lee Lin Lee, Taipei (TW); Ming-Tsung Kuo, Taipei (TW)

(73) Assignee: Bencha International Group Inc., Tortola (VG)

( * ) Notice: Subject to any disclaimer, the term of this patent is extended or adjusted under 35 U.S.C. 154(b) by 40 days.

(21) Appl. No.: 12/690,365

(22) Filed: Jan. 20, 2010

(65) Prior Publication Data

US 2010/0179486 A1    Jul. 15, 2010

Related U.S. Application Data

(63) Continuation-in-part of application No. 11/600,755, filed on Nov. 17, 2006, now Pat. No. 7,674,241.

(51) Int. Cl.
*A61M 5/32* (2006.01)

(52) U.S. Cl. ......... 604/195; 604/110; 604/111; 604/229

(58) Field of Classification Search .................. 604/110, 604/111, 195, 229
See application file for complete search history.

(56) References Cited

U.S. PATENT DOCUMENTS

| | | | |
|---|---|---|---|
| 5,053,010 A | 10/1991 | McGary et al. | |
| 6,086,568 A | 7/2000 | Caizza | |
| 6,368,303 B1 * | 4/2002 | Caizza | 604/110 |
| 6,393,898 B1 | 5/2002 | Hajduk et al. | |
| 6,585,690 B1 * | 7/2003 | Hoeck et al. | 604/110 |
| 6,689,106 B2 * | 2/2004 | Bush et al. | 604/181 |
| 6,752,782 B2 | 6/2004 | Liao | |
| 6,872,193 B2 * | 3/2005 | Shaw et al. | 604/164.07 |
| 6,966,898 B1 * | 11/2005 | Pouget et al. | 604/197 |
| 7,258,678 B2 | 8/2007 | Wilkinson et al. | |
| 2003/0045838 A1 * | 3/2003 | Woodard et al. | 604/218 |
| 2004/0153035 A1 * | 8/2004 | Shih | 604/197 |
| 2006/0111669 A1 * | 5/2006 | Kuan | 604/110 |
| 2007/0185458 A1 | 8/2007 | Lin Lee | |
| 2008/0097308 A1 * | 4/2008 | Schiller et al. | 604/110 |
| 2008/0306452 A1 * | 12/2008 | Crawford | 604/263 |

FOREIGN PATENT DOCUMENTS

| | | |
|---|---|---|
| CN | 2678668 Y | 2/2005 |
| CN | 100563740 C | 12/2009 |
| EP | 1192967 A1 | 4/2002 |
| TW | I294782 | 3/2008 |
| WO | WO2008037138 | 4/2008 |

OTHER PUBLICATIONS

U.S. Appl. No. 12/208,774, filed Sep. 11, 2008, Lin Lee Lee.

* cited by examiner

*Primary Examiner* — Jackie Ho
*Assistant Examiner* — Gerald Landry, II
(74) *Attorney, Agent, or Firm* — Ming Chow; Sinorica, LLC

(57) ABSTRACT

A safety injector comprises a needle hub attached by a needle, a hollow barrel for engaging with the needle hub and guiding the needle hub to retract into the hollow barrel, and a plunger combination settled in the hollow barrel. The plunger combination comprises a retractable plunger and a hollow plunger partially telescoped with the retractable plunger, wherein at least one raised portion is formed on an outer wall of the retractable plunger and at a telescoping portion for engaging at least one depression formed on an inner wall of the hollow plunger so that when the plunger combination continuously receives a pushing force after the safety injector is used to perform the injection operation, the retractable plunger can smoothly retract into the hollow plunger. Consequently, a space in the hollow barrel can be spared for accommodating the retracted needle hub.

18 Claims, 30 Drawing Sheets

AUTOMATICALLY RETRACTABLE SAFETY INJECTOR FOR NON-LIQUID MATERIAL

This application is a continuation-in-part application of, and claims the benefit of priority from, the U.S. patent application Ser. No. 11/600,755 filed on Nov. 17, 2006, now U.S. Pat. No. 7,674,21 the contents of which are incorporated by reference.

BACKGROUND OF THE INVENTION

1. Technical Field

The present invention relates to safety injectors and, more particularly, to an automatically retractable safety injector and a plunger combination which is one-hand operatable and functions for automatically retracting a needle thereof after the injection is completed to prevent needlestick injury.

2. Description of Related Art

For purposes of avoiding the risk of cross-infection of infectious disease such as AIDS, Hepatitis B, and Hepatitis C; precluding drug addicts from repeatedly using injectors; and protecting medical staff from being accidentally injured by used needles. There are many patents related to so called "safety syringe". However, most of such safety syringes are designed to be operated with two hands which is not easy and convenient for healthcare worker to use. Even with one hand, the user has to exert a force thereon during injection operation in a way that the syringe requires holding at a specific angle. Consequently, the two-handed operated safety syringes are not preferred by the healthcare works, because there are more risks of needlestick injury than one-handed operated safety syringe.

With attempts to mend the aforementioned problem, Taiwan Patent Publication Number 520995, which is entitled as "Automatically Retractable Safety Injector" and U.S. Pat. No. 6,712,793 B1, which is entitled as "Needle Guard Assembly for the Needle of A Syringe Body", each suggests a novel and one-hand operatable safe syringe. As shown in FIGS. 1A and 1B, the syringe of prior arts comprises a hollow barrel 12', a needle hub 11' for engaging a needle 10', an annular retracting spring 13' and a breakable retracting plunger 14'. Therein, the breakable retracting plunger 14' including a proximal part 17', a breakable connection 18', and a hollow distal part 19', which are formed integrally as one piece. After the breakable retracting plunger 14' is assembled into the hollow barrel 12' and used to perform liquid-drug injection operation by a user, the user can continue pushing the breakable retracting plunger 14' toward the needle 10' to break the breakable connection 18', so that the proximal part 17' can retract into the hollow distal part 19'. As a result, space in the hollow barrel 12' can be partially spared such that the needle hub 11' can lead the used needle 10' to be accommodated in the hollow barrel 12' together.

However, to facilitate users' exerting force and ensure practicability of the above-mentioned breakable retracting plunger, there are strict requests for symmetry and precision of the breakable connection of the plunger. Consequently, the dimensional tolerance for the molds used to form the one-piece plunger through injection molding process is very small. Besides, the conventional plunger is liable to be broken during fabrication and transportation. Therefore, the yield rate and output are significantly limited while the costs of molds are unavoidably high. Further, with the precise design, safety function of retraction of such conventional plunger can only be effective when the plunger is operated at a predetermined force-exerting angle. Thus, when the prior syringe is implemented to inject a patient at his/her curved-contour skin portion or his/her delicate apparatus, such as the head, post-auricular, eyes, or oral skin, it is difficult for a medical staff member to operate the syringe with his/her single hand. Moreover, clumsy operation due to the limited force-exerting angle can accidentally damage the syringe and cause discomfort to the patient.

SUMMARY OF THE INVENTION

The present invention has been accomplished under these circumstances in view. It is one objective of the present invention to provide a safety injector and a plunger combination thereof which facilitate one-hand operation and eliminate the liability to being damaged during injection operation by a user's inexact force-exerting angle and posture.

It is another objective of the present invention to provide a safety injector and a plunger combination thereof which eliminate the liability to being damaged during fabrication, for purposes of enhancing the quality and yields rate, improving the reliability, and reducing material waste and processing costs of the disclosed subject matter.

It is another objective of the present invention to provide a safety injector and a plunger combination thereof which can be easily made through plastic injection molding process, so as to ease the dimensional request for the precision of the molds for producing injectors and rationalize the dimensional tolerance, such that the manufacturing costs of the disclosed subject matter can be reduced.

It is another objective of the present invention to provide a safety injector and a plunger combination thereof which have functions of buffing received force and resisting transverse shear, in order to provide enhanced convenience to a user's injection operation and decrease failure rate of injection operation as well as patient pain.

It is another objective of the present invention to provide a safety injector for injecting non-liquid materials into human or animal bodies for medical or non-medical purposes, such as implant subcutaneously a solid medicine or biological chips.

It is yet another objective of the present invention to provide a safety injector and a plunger combination thereof which can be molded with increased output of single batch so as to significantly enhance the output of the disclosed subject matter.

It is still another objective of the present invention to provide a safety injector and a plunger combination thereof wherein a plunger thereof is made with present mechanical strength and desirable practicability so as to facilitate retracting a used needle thereof.

To achieve these and other objectives of the present invention, the automatically retractable safety injector and the plunger combination thereof are disclosed for single use of intramuscular injection, subcutaneous injection or intravenous injection with liquid or non-liquid materials for medical or non-medical purposes.

The safety injector comprises a needle hub attached with a needle, a hollow barrel engaging with the needle hub and guiding the needle hub to retract into the hollow barrel after the safety injector is used to perform an injection operation, and a plunger combination settled in the hollow barrel. The plunger combination includes a retractable plunger and a hollow plunger partially telescoped with the retractable plunger. At least one raised portion is provided on an outer surface of the retractable plunger at a telescoping portion where the retractable plunger is partially telescoped with the hollow plunger for wedging at least one depression formed on an inner surface of the hollow plunger. Thereupon, when a user continues pushing the plunger combination after the injector is used for injection operation, the retractable plunger can retract into the hollow plunger, so as to spare space in the hollow barrel for accommodating the used needle hub.

According to one concept of the present invention, in the plunger combination of the safety injector, the hollow plunger and the retractable plunger can be positionally exchanged. Particularly, to achieve optimal effect of retraction of the retractable plunger, the present invention discloses one or more transverse stress adjustable notches, which are positioned at a center of the retractable plunger and at the telescoping portion where the retractable plunger is partially telescoped with the hollow plunger, and at least one stress adjustable notch, which is arranged on an inclined edge of the hollow plunger and has a lengthwise depth not reaching the depression on the inner surface of the hollow plunger.

The present invention further provides a reinforcing design for the retractable plunger and the hollow plunger of the plunger combination of the present invention for harmonizing with force strength of one-hand operation and various force-exerting angles.

In a second embodiment of the present invention, an automatically retractable safety injector and a plunger combination thereof according to the present invention are provided with one or more exhausting opening formed on a lateral wall of the hollow plunger and positioned distant from the needle or on the wings, so that when the retractable plunger retracts into the hollow plunger, the exhausting opening formed on the hollow plunger or on the wings properly functioning for exhausting air so as to avoid air drag hindering a pushing operation of a user's thumb and facilitate the user's injection operation. Similarly, when the retractable plunder of the plunger combination is positioned near a rear end of the hollow barrel, one or more exhausting opening may be formed on a lateral wall of the retractable plunder and positioned distant from the needle, so that desirable effect of air exhausting can be performed by the exhausting opening In a third and a fourth embodiments of the present invention, at least one transversely convex annular rib or one or more ranks of transversely convex dots, which are arranged adjacently or alternately, may be formed on the outer surface of the retractable plunger instead of the aforementioned raised portions. Correspondingly, at least one concave annular rib or one or more ranks of annular grooves, which are arranged adjacently or alternately, may be formed on the inner surface of the hollow plunger instead of the aforementioned depressions.

Further, in a fifth embodiment of the present invention, at the telescoping portion of the retractable plunger and the hollow plunger, a plurality of stoppers are formed on the lateral wall of the hollow plunger adjacent to a lower edge of the retractable plunger and arranged along a direction where the retractable plunger retracts. Alternatively, a rough region is provided on the retractable plunger above the raised portions, as shown in a sixth embodiment, whereby an excessive pushing force from a user acting on the plunger can be neutralized or buffed, so that the retractable plunger can be prevented from prematurely retracting into the hollow plunger before completion of injection operation and therefore successful injection operation can be ensured.

For improving yield rate and user practicability of the disclosed safety injector and the plunger combination thereof, an improved design is applied to the needle hub. As described in a seventh embodiment, a narrow barrel having a diameter smaller than that of the hollow barrel is integrally formed with the hollow barrel at a front end of the hollow barrel for accommodating a compressed spring and a portion of the needle hub so as to enhance the retraction of the needle hub. Therein, at least one hollow stopper (movable retaining ring) is provided around an opening of the hollow barrel where the hollow barrel borders on the narrow barrel, and an inner diameter of a hollow portion of the stopper is smaller than a diameter of part of the needle hub so as to prevent the needle hub from falling off outward when receiving an excessive pushing force during injection operation and to guide the needle hub to retract after injection operation is completed.

In addition to the hollow stopper, a neck portion disclosed by an eighth embodiment of the present invention is formed integrally with an opening of the narrow barrel while the hollow barrel is molded through injection molding process. The neck portion is formed with a through hole at a center thereof in a manner that only the needle and part of the needle hub are allowed to pass therethrough, whereby the needle hub can be also retained and a stretching length of the needle hub from the neck portion can be controlled for optimum retraction of the needle hub.

Instead of the integrally formed breakable connection used in the prior arts, a split design is applied to the automatically retractable safety injector and the plunger combination of the present invention. The retractable plunger and the hollow plunger, which are made of a flexible material such as plastic or rubber, are separately produced by injection molding process and then assembled together. Thus, risks of accidentally damaging the plunger during fabrication and failed injection operation caused by the damaged plunger damaged before and during injection operation can be reduced. Besides, since the two-piece plunger can have components thereof separately molded and then assembled, required dimensional precision of molds can be lower than that of the one-piece plunger having the breakable connection wherein mechanical balance of the connected portion thereof has to be taken into consideration. As a result, design and manufacturing costs of the molds are reduced while the reliability and the quality stability of the products are enhanced.

On the other hand, the two-piece plunger combination surpasses the breakable connection used in the plunger of the prior syringe in mechanical balance property for resisting transverse shear. Therefore, when a patient uses his/her single hand to inject himself/herself, or when a medical staff member injects a patient at his/her body portion unfavorable to force exerting, the practicability of the disclosed subject matter is not deteriorated by the limitation of force-exerting angle or posture.

BRIEF DESCRIPTION OF THE DRAWINGS

The invention as well as a preferred mode of use, further objectives and advantages thereof, will best be understood by reference to the following detailed description of an illustrative embodiment when read in conjunction with the accompanying drawings, wherein.

DETAILED DESCRIPTION OF THE PREFERRED EMBODIMENT

Some particular embodiments of the invention will be described in detail for purpose of illustration, and one of ordinary skill in the art can easily understand the advantages and efficacy of the present invention through the disclosure of the specification. It is to be understood that alternative embodiments may be possible for the implement and application of the present invention while numerous variations will be possible to the details disclosed in the specification on the strength of diverse concepts and applications without going outside the scope of the invention as disclosed in the claims.

Figure 1A:
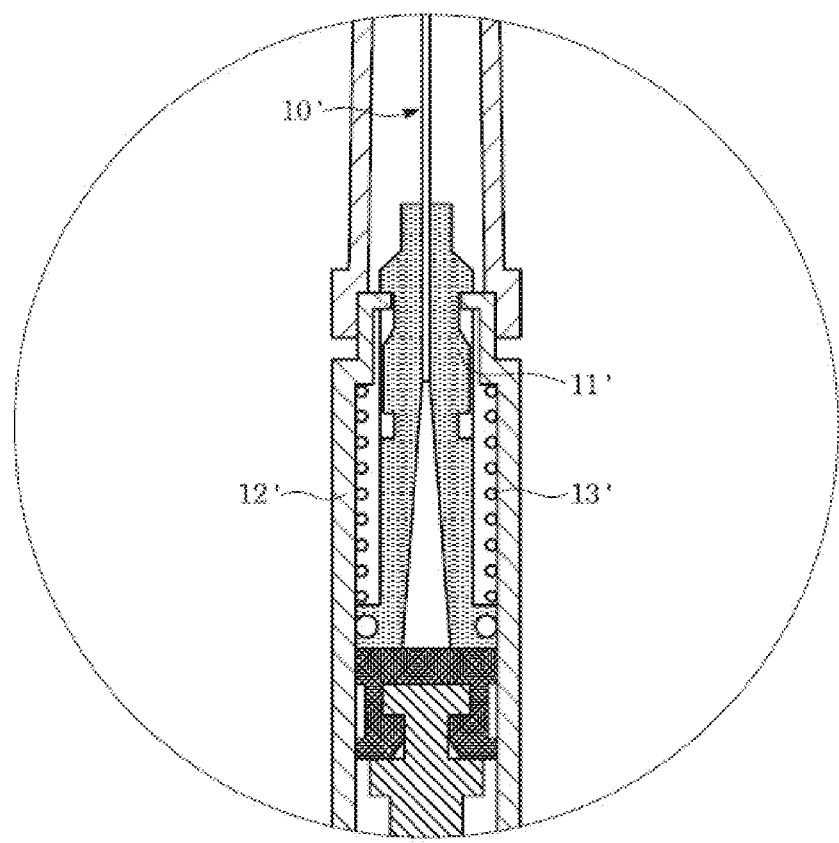
FIGS. 1A and 1B are a cross sectional view and a partial cross sectional view of a conventional automatically retractable safety injector.
Figure 1B:
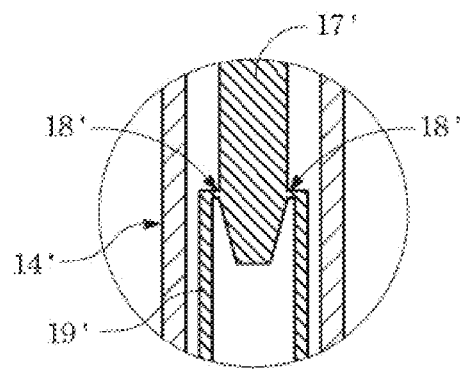
Figure 2:
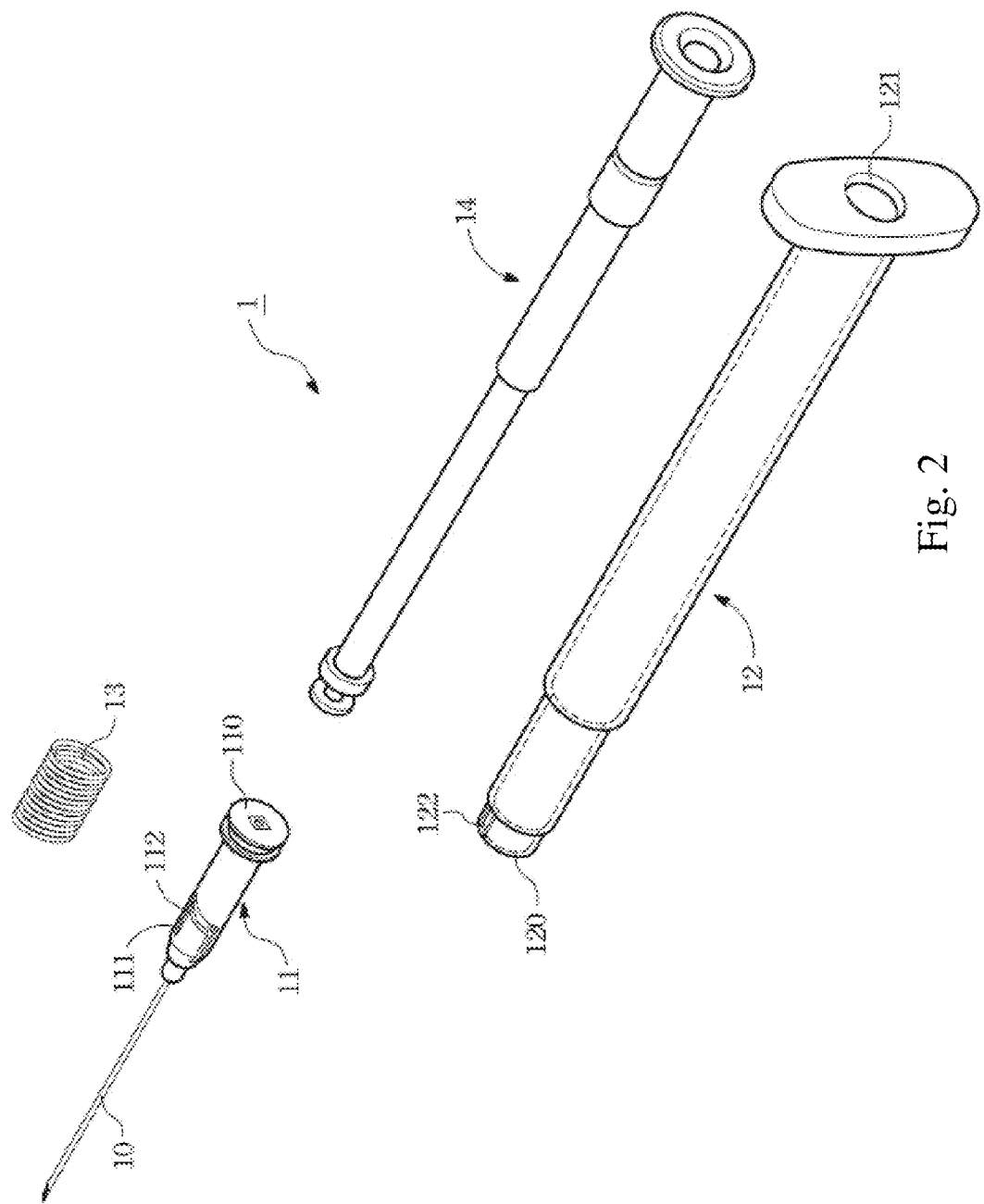
FIG. 2 is an extended view of a safety injector and a plunger combination according to a first embodiment of the present invention.
Figure 3A:
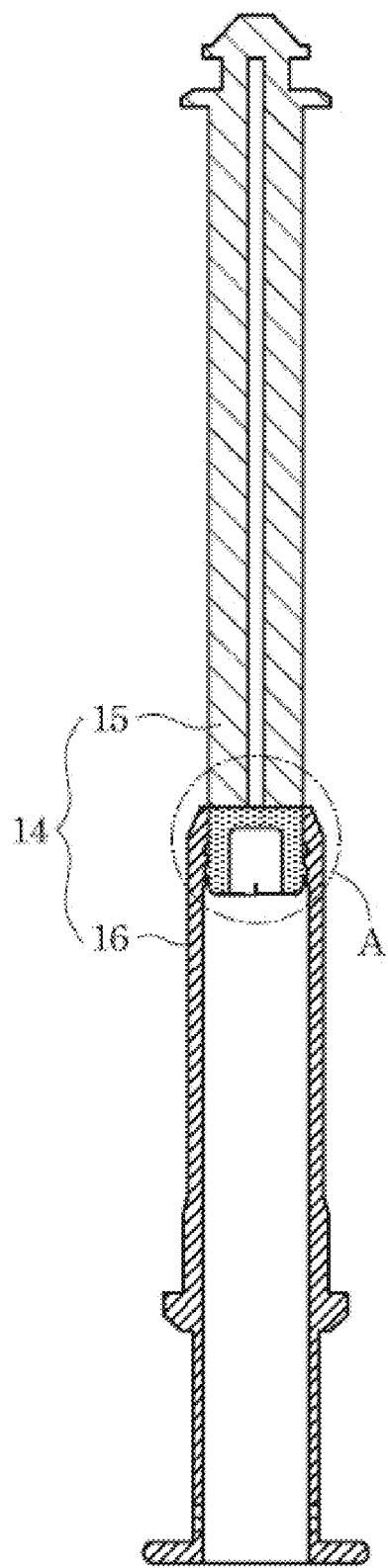
FIGS. 3A and 3B include a cross sectional view and a partial enlarged cross sectional view of the plunger combination according to the first embodiment of the present invention.
Figure 3B:
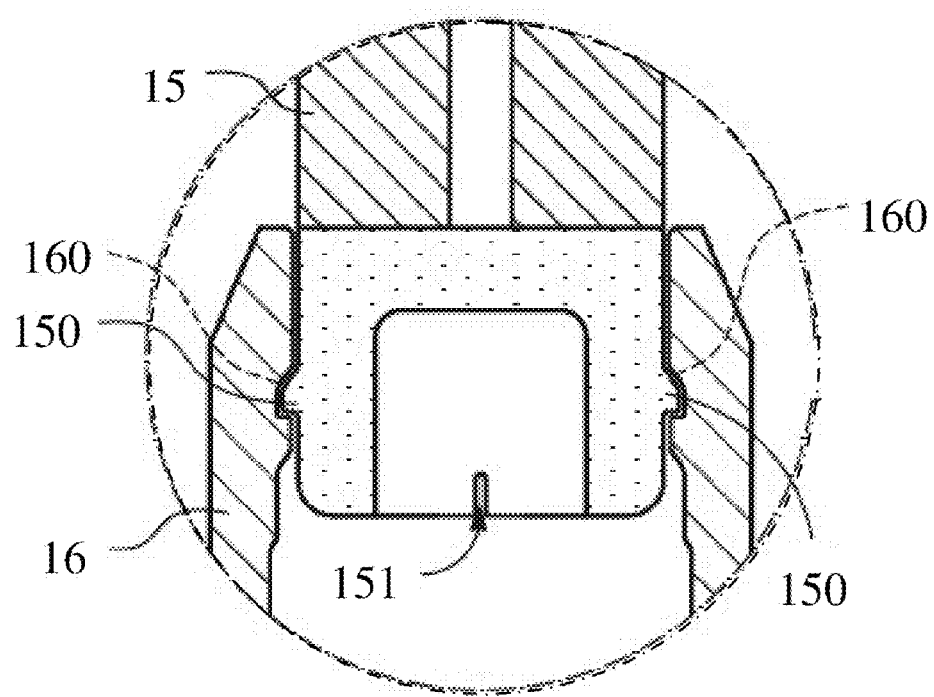
Figure 4:
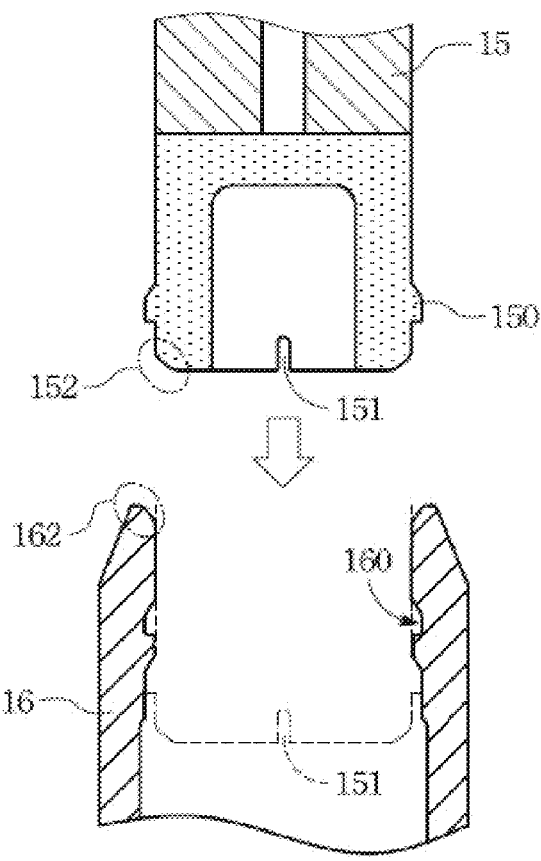
FIG. 4 is a schematic drawing showing a retractable plunger and a hollow plunger of the plunger combination partially telescoped according to the first embodiment of the present invention.

FIGS. 2, 3, and 4 are respectively an extended view, cross sectional views and schematic drawing of an automatically retractable safety injector and a plunger combination thereof for single use of muscle injection, hypodermic injection or intravenous injection with liquid medical drug or blood drawing according to the present invention. It is to be noted that the recited drawings are simplified for conceptually illustrating the embodiments of the present invention. Components shown in the drawings are not necessarily the actual forms of the implement of the present invention. The numbers, shapes and dimensional scales of the components of the present invention may be embodied with a selective design and typically with a more complex arrangement.

Referring to FIG. 2, according to a first embodiment of the present invention, the disclosed automatically retractable safety injector 1 comprises at lease: a needle hub 11 attached with a needle 10, a hollow barrel 12, and a plunger combination 14 settled in the hollow barrel 12. The hollow barrel 12 engages with the needle hub 11 and at least one annular retracting spring 13 is implemented to guide the needle hub 11 to retract along a direction opposite to a direction where the needle hub moves during injection operation.

Particularly, the needle hub 11 has one end thereof accommodating the needle 10 that penetrates a center of the needle hub 11 and has an opposite end provided with a disc 110 for receiving the compressed annular retracting spring 13. Pluralities of positioning grooves 111 and U-shaped slide passages 112 contacting the positioning grooves 111 are disposed at proper positions between the two ends of the needle hub 11. The positioning grooves 111 are used to engage with a front end 120 of the hollow barrel 12 so that when the annular retracting spring 13 is released from a compressed position, the needle hub 11 is released from the front end 120 of the hollow barrel 12 and retracts along the U-shaped slide passages 112 toward the direction opposite to the direction where the needle hub moved during injection operation. By adjusting the U-shaped slide passages 112, a distance where the needle hub 11 retracts for can be controlled to prevent the needle 10 from jutting out the hollow barrel 12. However, any component that has elastic recovery property and can be compressed and released, such as a metal leaf spring, may be used as an equivalent substitute of the annular retracting spring 13.

Further, as shown in FIG. 2, the hollow barrel 12 has the front end 120 and a rear end 121. A plurality of elastic retaining hook 122, which are slightly flexible, are deposited at the front end 120 of the hollow barrel 12 in a manner that the elastic retaining hooks 122 face a center of the hollow barrel 12. When the disclosed subject matter is in an original state before being used and during injection operation, the elastic retaining hooks 122 firmly engage with the positioning grooves 111 of the needle hub 11. When a user continues pushing the plunger combination 14 toward the needle 10 after completion of injection operation, the elastic retaining hooks 122 are indirectly pressed and flexibly expanded so that the needle hub 11 can detach from the elastic retaining hooks 122 and retract into the hollow barrel 12.

Please refer to FIGS. 3A and 3B. According the first embodiment of the present invention, the disclosed automatically retractable safety injector 1 is characterized by a novel design of the plunger combination 14. As shown in the drawing, the plunger combination 14 has a two-piece structure and is composed of a retractable plunger 15 and a hollow plunger 16, which are separately molded through injection molding process and then assembled together. Therein, a bottom of the retractable plunger 15 is placed inside the hollow plunger 16. Further, as shown in FIG. 3B (i.e. a telescoping portion A of FIG. 3A), a plurality of raised portions 150 are formed an outer surface of the retractable plunger 15 while a plurality of depressions 160 are formed on an inner surface of the hollow plunger 16 positionally corresponding to the raised portions 150. When the plunger combination 14 is in the original state before being used or during injection operation, the raised portions 150 of the retractable plunger 15 firmly engage with the depressions 160 of the hollow plunger 16. When a user continues pushing the plunger combination 14 toward the needle 10 after completion of injection operation, the raised portions 150 are forced to depart from the depressions 160 so that the retractable plunger 15 can retract into the hollow plunger 16, and space in the hollow barrel 12 initially occupied by the retractable plunger 15 can be spared for accommodating the retracted needle hub 11 (as shown in FIG. 2).

Furthermore, the retractable plunger 15 or the hollow plunger 16 depicted in FIG. 3A is made of a slightly flexible material, such as polyethylene (PE), polyvinyl chloride (PVC) or rubber, or a transparent rigid plastic, such as polypropylene (PP) or an AN series plastic and molded through injection molding process. In virtue of stiffness provided by the transparent rigid plastic, the retractable plunger 15 and the hollow plunger 16 can bear desirable injecting force. According to the present embodiment, a trunk portion of the retractable plunger 15 can be shaped as a lengthwise cross rib or a column.

Referring to FIG. 3B, in order to maintain balancing of stresses on the plunger combination 14, the present embodiment provides a modified mode. That is, one or more transverse stress adjustable notches 151, which are positioned at a center of the retractable plunger 15 and at the telescoping portion A where the retractable plunger 15 and the hollow plunger 16 are partially telescoped. The transverse stress adjustable notches 151 may be caves, blind holes or through holes. Generally, each of the transverse stress adjustable notches 151 has a lengthwise depth not approaching or reaching a position where the raised portions 150 are formed on the outer surface of the retractable plunger 15. Thereupon, when the plunger combination 14 is continuously pushed after completion of injection operation, the transverse stress adjustable notches 151 can become deformed so as to make the raised portions 150 detach from the depressions 160.

Furthermore, the raised portions 150 in the present embodiment may be a plurality of raised dots integrally formed on the retractable plunger 15 when the retractable plunger 15 is molded through injection molding process. Shapes, dimensions, amounts and arrangement of the raised dots are not to be limited by the present embodiment. However, in the present embodiment, six pairs of symmetrically arranged raised dots are implemented as a preferable embodying mode while a plurality of convex annular ribs may be also used as equivalent substitutes of the raised portions 150 described in the present embodiment.

Please refer to FIG. 4 for the structure of the hollow plunger 16. To make the hollow plunger 16 partially telescope and firmly engage with the retractable plunger 15, the plurality of depressions 160 are formed on the inner wall of the hollow plunger 16 near where the hollow plunger 16 partially telescopes the retractable plunger 15 for engaging the plurality of raised portions 150. The depressions 160 may be recesses, dents or partial or intact concave annular ribs and the depressions 160 may have C-shaped, chamfered rectangular, or irregular sectional shapes. Actually, depressions having any sectional shapes may be equivalent substitutes of the depressions 160 of the present embodiment, as long as the sectional shapes thereof can firmly engage with the raised portions 150 of the retractable plunger 15. However, in the present embodiment, intact concave annular ribs are implemented as a preferable embodying mode. Thereby, rotation of the retractable plunger 15 is not hindered by geometric positions of the raised portions 150 when the retractable plunger 15 is assembled to the hollow plunger 16.

From FIG. 4, the retractable plunger 15 has a lower edge 152 thereof below the raised portions 150 chamfered while the hollow plunger 16 has an upper edge 162 formed as a cambered, chamfered or inclined surface Therefore, an inner diameter of the upper edge 162 of the hollow plunger 16 can be equal to or greater than an outer diameter of the lower edge 152 of the retractable plunger 15. Hence, when the raised portions 150 are detached from the depressions 160 after completion of injection operation, the retractable plunger 15 can slide into the hollow plunger 16 and perform retraction smoothly.

Figure 5:
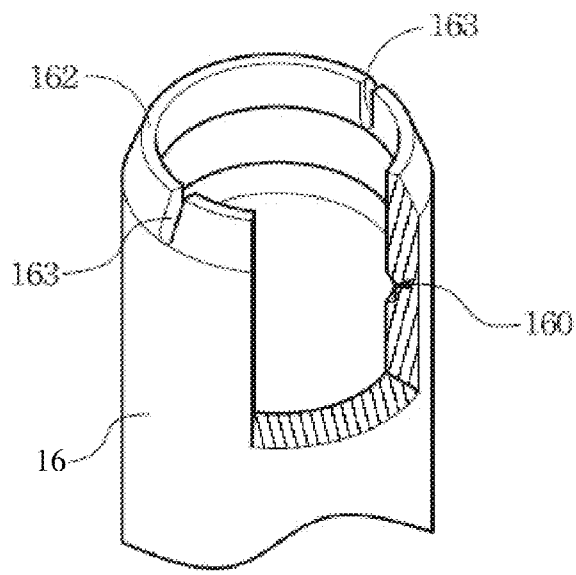
FIG. 5 is a perspective view of the hollow plunger in the safety injector according to the first embodiment of the present invention.

When the plunger combination 14 is put into practical manufacture, strength of retracting and pulling forces of the retractable plunger 15 and the hollow plunger 16 have to meet specific mechanical test standards. Thus, as shown in FIG. 5, the first embodiment of the present invention further discloses another modified mode, wherein at least one stress adjustable notch 163 is additionally formed on the inclined upper edge 162 of the hollow plunger 16. The stress adjustable notch 163 has a lengthwise depth not reaching the depressions 160 on the inner surface of the hollow plunger 16 and may be, for example, a cave or a blind hole.

According to the present invention, in the plunger combination 14 of the safety injector 1, the hollow plunger 16 and the retractable plunger 15 can be positionally exchanged. No apparent limitation of relative position of the two components is made in the present embodiment. In addition to the arrangement that the retractable plunger 15 is positioned near the needle hub 11 so that a direction where the retractable plunger 15 retracts after completion of injection operation is coordinated to a direction where the needle hub 11 retracts after the needle hub 11 is detached, in an alternative embodiment as described below, the retractable plunger 15 is positioned at a rear portion of the hollow barrel 12 and distant from the needle hub 11.

Now please refer to FIG. 6A to 6D. A plunger combination 14 is a two-piece combination composed of a retractable plunger 15 and a hollow plunger 16. A plurality of raised portions 150 are formed an outer surface of the retractable plunger 15 while a plurality of depressions 160 are formed on an inner surface of the hollow plunger 16 positionally corresponding to the raised portions 150. When the plunger combination 14 is in an original state before being used or during injection operation, the raised portions 150 of the retractable plunger 15 firmly engage with the depressions 160 of the hollow plunger 16. The difference between the present embodying mode and the aforesaid embodying mode is that the retractable plunger 15 and the hollow plunger 16 are positionally exchanged. When a user continuously pushes the plunger combination 14 toward the needle 10 after completion of injection operation, the raised portions 150 formed on a top portion of the inner wall of the retractable plunger 15 are forced to detach from the depressions 160 so that the retractable plunger 15 can retract into the hollow plunger 16.

Figure 6A:
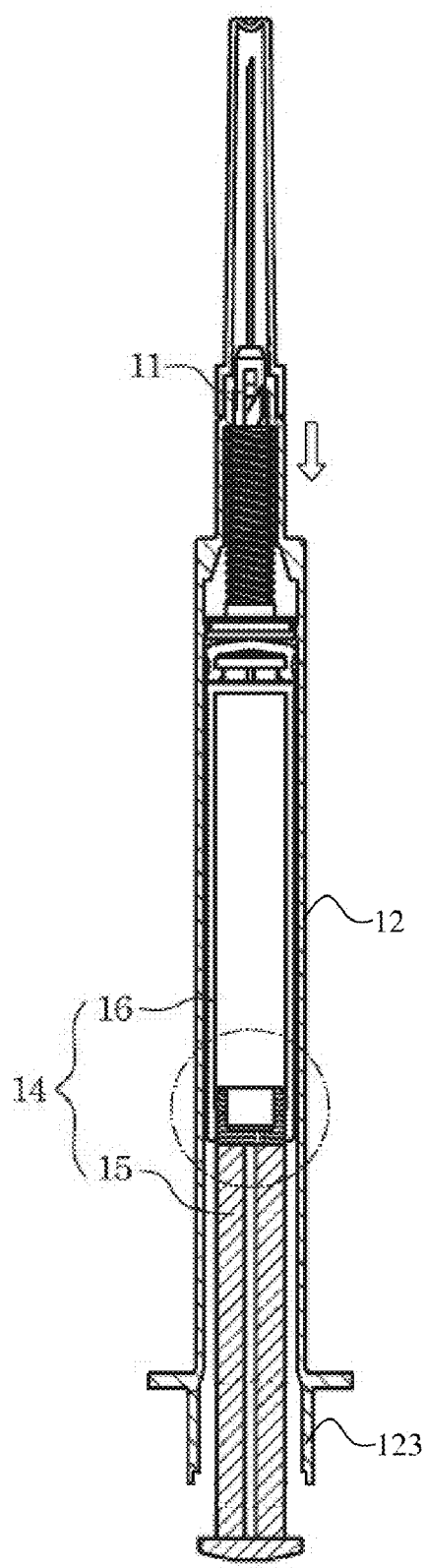
FIGS. 6A to 6D show an alternative embodying mode of the safety injector according to the first embodiment of the present invention.
Figure 6B:
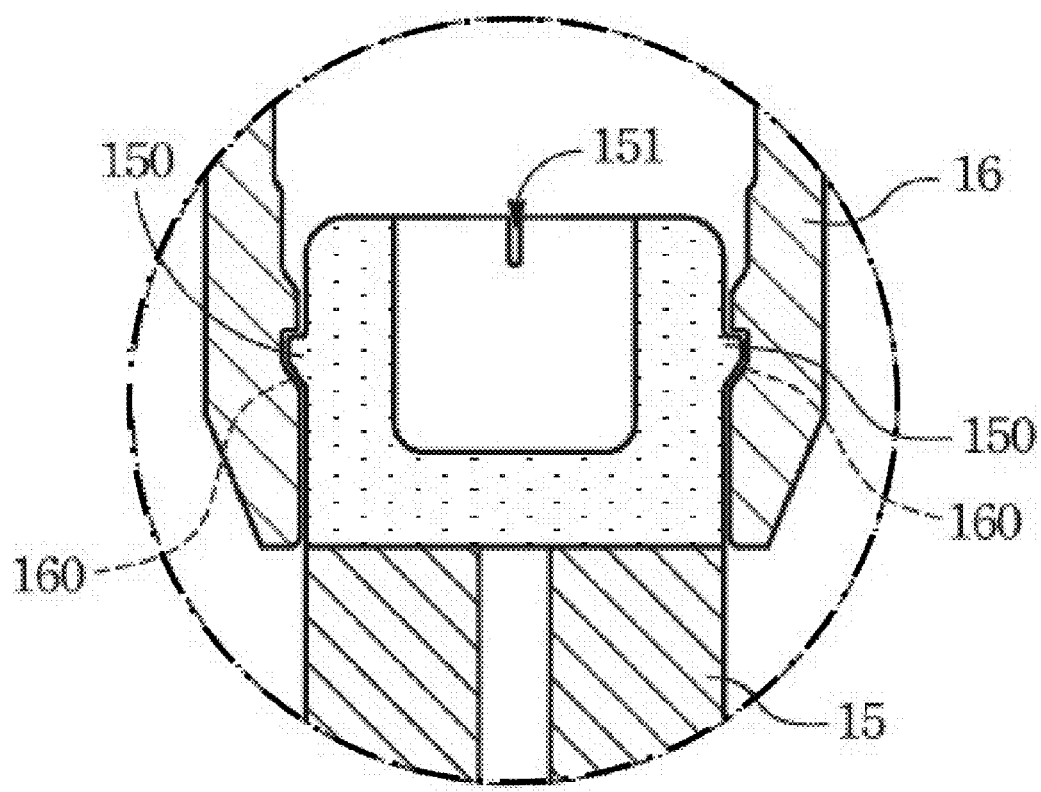
Figure 6C:
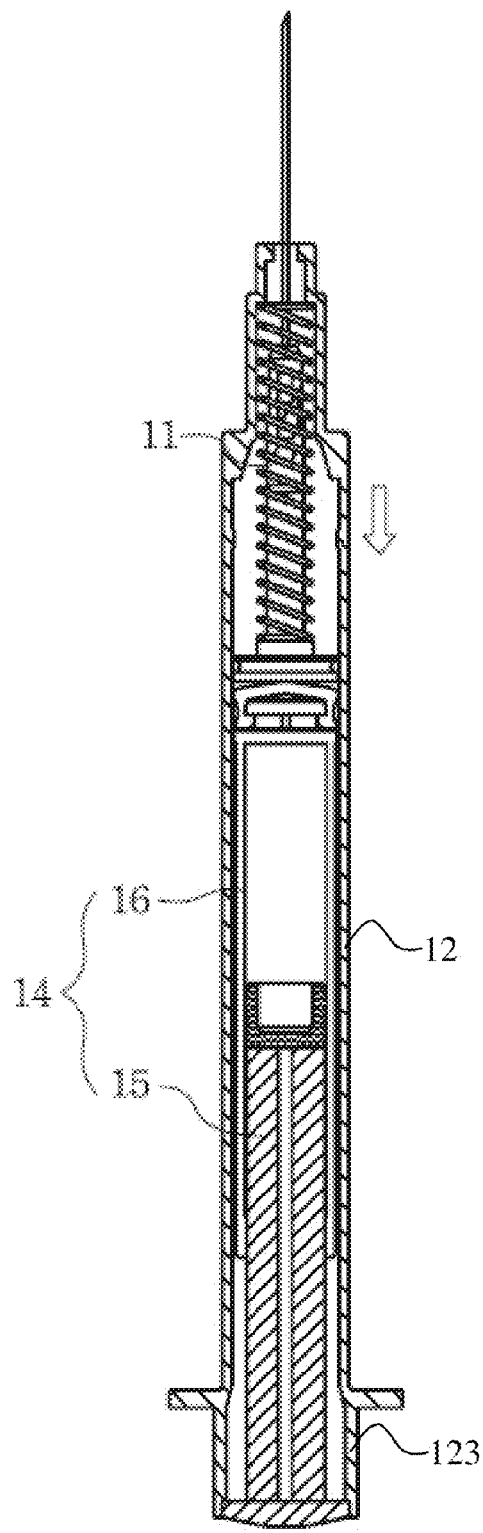
Figure 6D:
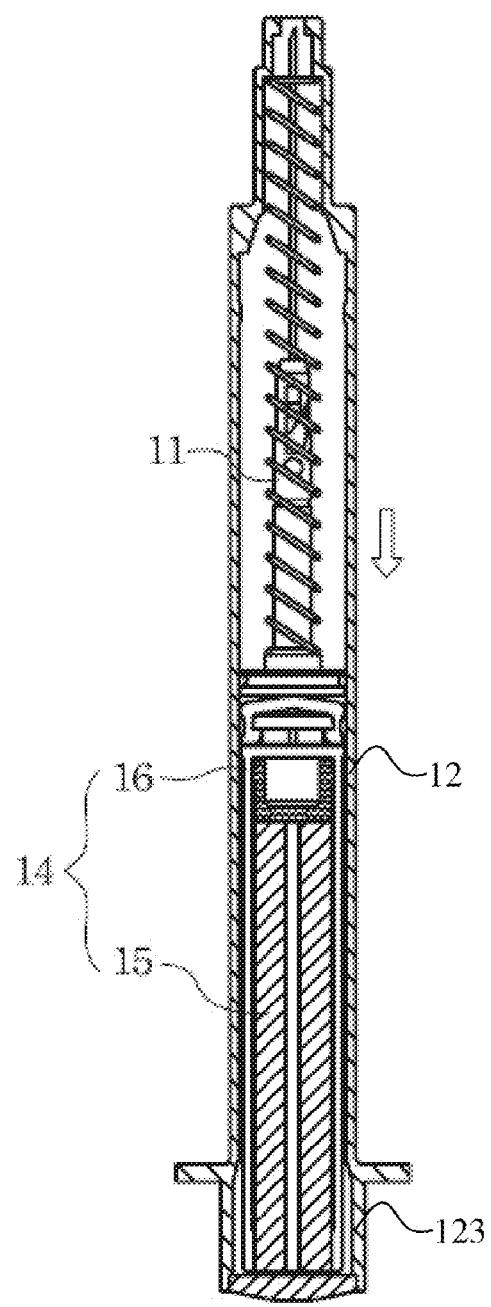

At this time, as shown in FIGS. 6C and 6D, a direction where the retractable plunger 15 retracts into the hollow plunger 16 is opposite to a direction where the needle hub 11 retracts into the hollow barrel 12 after the raised portions 150 detach from the depressions 160. Even, to ensure the preferable practicability for one-hand operation of the plunger combination 14 having the retractable plunger 15 positioned at the rear portion of the hollow barrel 12, a plurality of extending portions 159 may be provided at a rear end of the hollow barrel 12 and two sides of a bottom of the retractable plunger 15 for controlling a distance where the retractable plunger 15 retracts for so as to spare sufficient space in the hollow barrel 12 for accommodating the needle hub 11.

Besides, a wing 121 is formed on the distant end of the hollow barrel 12 as depicted in FIG. 6A so as to prevent users from pushing the retractable plunger 15 too further and resulting in the destruction of the plunger combination 14. Such configuration could also be applied in the aforementioned embodying mode that the retractable plunger 15 is positioned near the needle hub 11.

All the details described above are preferable embodying modes of the first embodiment of the present invention and not to be regarded as limitations to the present invention. Any plunger combination is a two-piece combination composed of a hollow plunger and a retractable plunger that are partially telescoped shall be considered as within the equivalent range of the present invention despite the modifications on sequence, combining means and segmental connection of the hollow plunger and the retractable plunger. Meanwhile, the present invention further provides a reinforcing design for the retractable plunger and the hollow plunger of the plunger combination for harmonizing with force strength of one-hand operation and various force-exerting angles.

FIGS. 7 through 14 illustrate alternative embodiments of the safety injector and the plunger combination thereof according to the present invention. While the alternative embodiments are different from the first embodiment with some particular components, the other components are substantially identical to those described in the first embodiment. Hence, the following descriptions will be only directed to the characteristics that distinguish the alternative embodiments from the first embodiment and those components identical to those described in the first embodiment will not be discussed at length.

Figure 7:
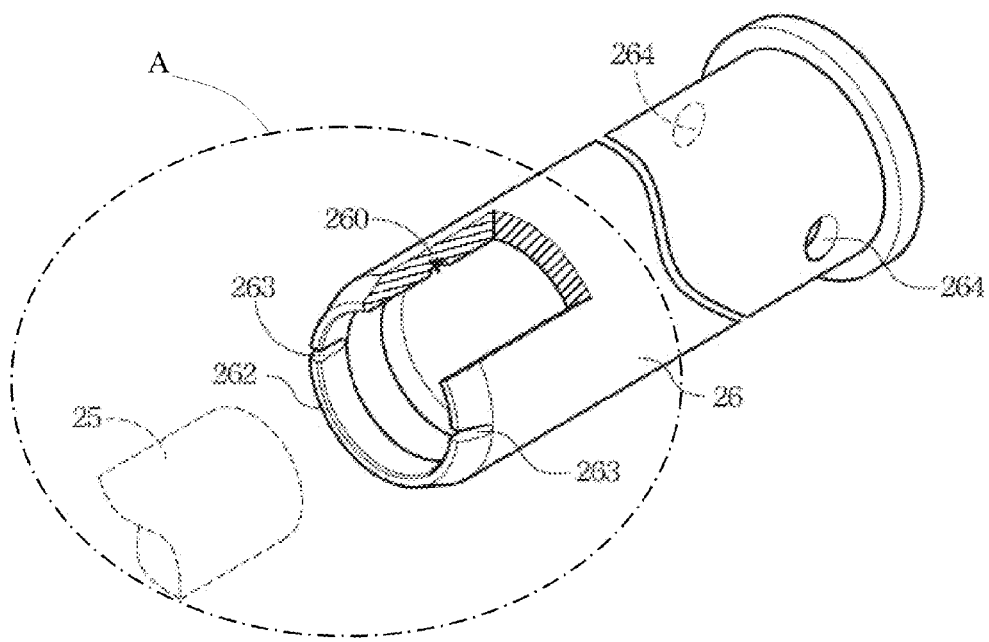
FIG. 7 is a partially sectioned perspective view of a hollow plunger in a safety injector according to a second embodiment of the present invention.

FIG. 7 illustrates a second embodiment of a safety injector and a plunger combination thereof according to the present invention. As shown in the drawing, a hollow plunger 26 of the plunger combination is provided with one or more exhausting opening 264 formed on a lateral wall of the hollow plunger 26 and positioned distant from the telescoping portion as shown in FIGS. 3A and 3B. Thereupon, when a retractable plunger 25 retracts into the hollow plunger 26, air drag can be eliminated through the exhausting opening 264 and does not hinder pushing operation of a user's thumb so as to facilitate the user's operation. In the present embodiment, a concave annular rib 260 is used instead of the depressions 160 used in the first embodiment while an upper edge 262 and stress adjustable notches 263 used herein are similar to the upper edge 162 and the stress adjustable notches 163 used in the first embodiment.

Figure 8:
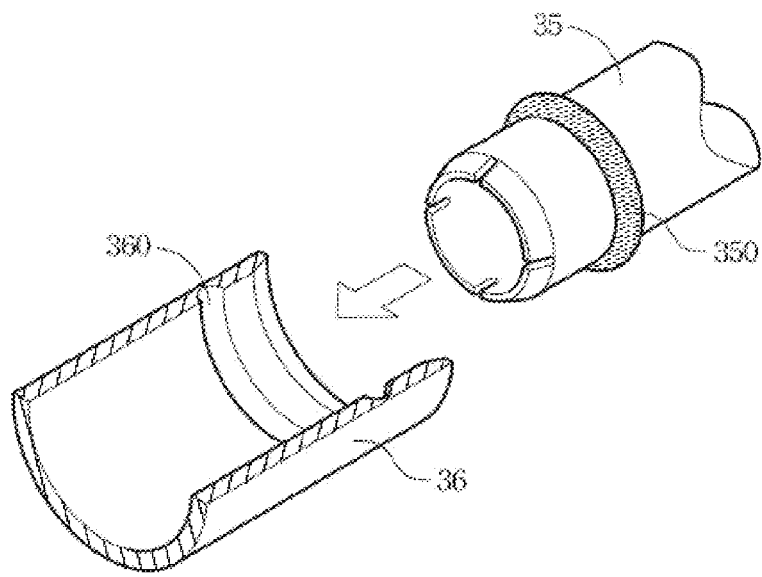
FIG. 8 is a partially sectioned perspective view of a plunger combination in a safety injector according to a third embodiment of the present invention.

Please refer to FIG. 8. In a third embodiment of a safety injector and a plunger combination thereof according to the present invention, a transversely convex annular rib 350 having a continuous or intermittent contour is formed on an outer of a retractable plunger 35 instead of the raised portions 150 of the first embodiment. Meanwhile, a concave annular rib 360 having a continuous or intermittent contour or one or more ranks of annular grooves each having a continuous or intermittent contour are formed on the hollow plunger 36 instead of the depressions 160 used in the first embodiment. The convex annular rib 350 and the concave annular rib 360 may be provided in a form of a single rank, respectively, or may be in a form of multiple ranks, respectively, as disclosed by a forth embodiment of a safety injector and a plunger combination thereof according to the present invention, which is shown in FIG. 9.

Figure 9:
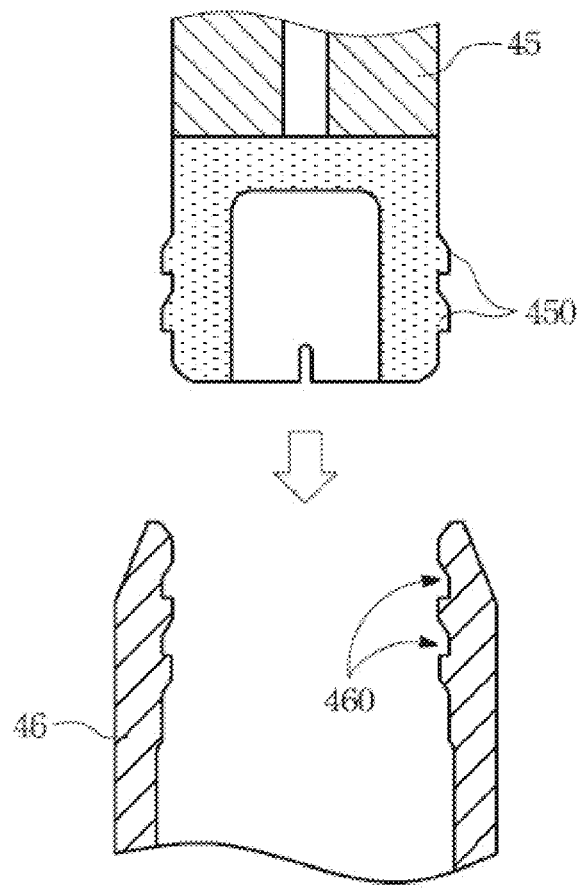
FIG. 9 is a partial cross sectional view of a plunger combination in a safety injector according to a fourth embodiment of the present invention.

According to the forth embodiment shown in FIG. 9, plural ranks of transversely convex annular ribs 450 each having a continuous or intermittent contour are arranged in a vertically adjacent or alternate manner on an outer surface of a retractable plunger 45 so as to replace the raised portions 150 of the first embodiment. Correspondingly, plural ranks of concave annular ribs 460 each having a continuous or intermittent contour are arranged in a vertically adjacent or alternate manner on an inner surface of the hollow plunger 46 so as to replace the depressions 160 used in the first embodiment.

On the other hand, to make the retractable plunger of the plunger combination meet specific mechanical requests for strength of pulling and retracting forces, the present invention further provides an improvement structure below the above-mentioned depressions or concave annular ribs or annular grooves of the hollow plunger.

Figure 10:
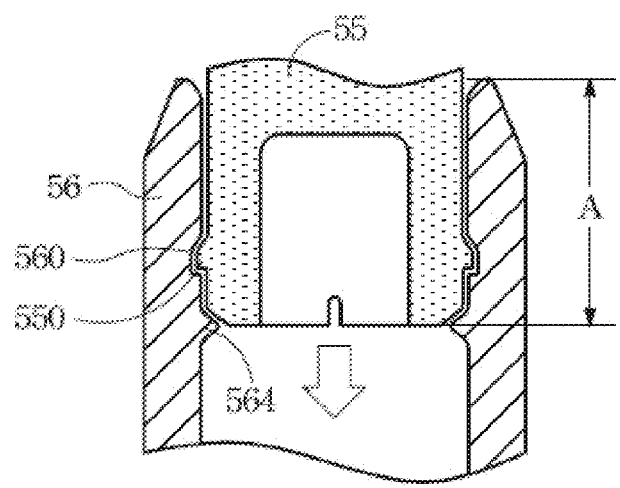
FIG. 10 is a partial cross sectional view of the plunger combination in a safety injector according to a fifth embodiment of the present invention.

In FIG. 10, a fifth embodiment of a safety injector and a plunger combination according to the present invention is illustrated. Therein, a plurality of stoppers 564 are formed at the telescoping portion A and near a lower edge of a depression or a concave annular rib or a annular groove 560 deposited on an inner wall of a hollow plunger 56 along a direction where a retractable plunger 55 retracts. The stoppers 564 contribute to an enhanced counterforce of the retractable plunger 55 during injection operation so that the retractable plunger 55 and the hollow plunger 56 can be combined with enhanced firmness. Therein, the stoppers 564 may be raised portions formed integrally with the hollow plunger 56 through injection molding process or affixed blocks. Further, the stoppers 564 each having an extending surface perpendicular to a lengthwise axis of the hollow plunger 56 or inclined along a direction coordinated to a direction where the retractable plunger 55 retracts.

Figure 11:
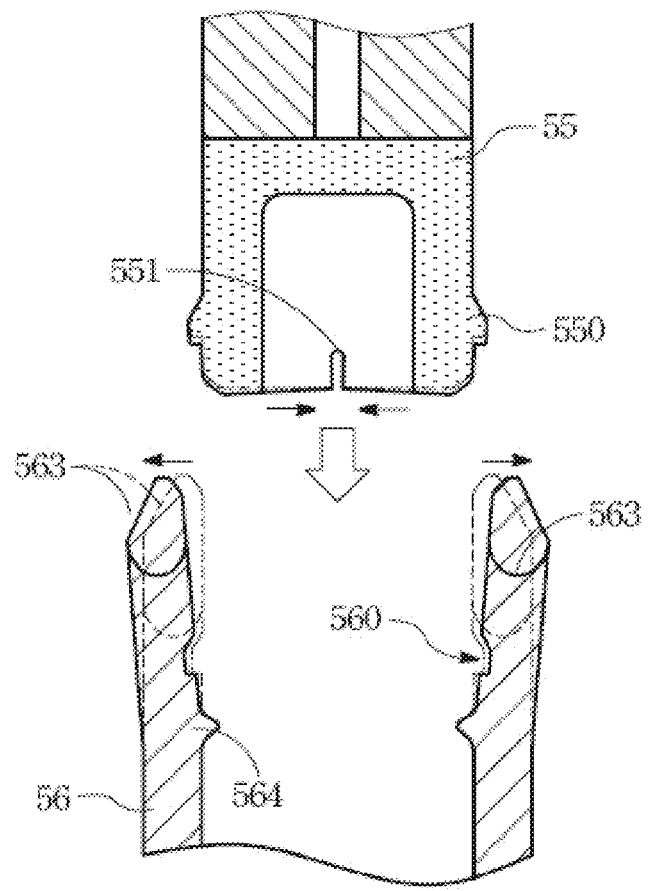
FIG. 11 is a schematic drawing showing in a safety injector, a retracting plunger retracting into a hollow plunger according to the fifth embodiment of the present invention.

In the fifth embodiment, the stoppers 546 are designed as having the extending surfaces inclined along the direction coordinated to the direction where the retractable plunger 55 retracts. Thus, as shown in FIG. 11, when a user continues pushing the plunger combination after liquid drug is fully injected, the raised portions 550 of the retractable plunger 55 are transversely compressed toward a stress adjustable notch 551 to synchronously enter into the hollow plunger 56. At this time, the downward inclined extending surface of the stoppers 564 can guide the retractable plunger 55 to slide downward smoothly. In addition, as the hollow plunger 56 is made of the slightly flexible material, the user's pushing force acting on the plunger combination can make stress adjustable notches 563 provided on an upper edge of the hollow plunger 56 fleetingly expanded in a transverse direction so that the retractable plunger 55 can retract into the hollow plunger 56 easier.

Figure 12:
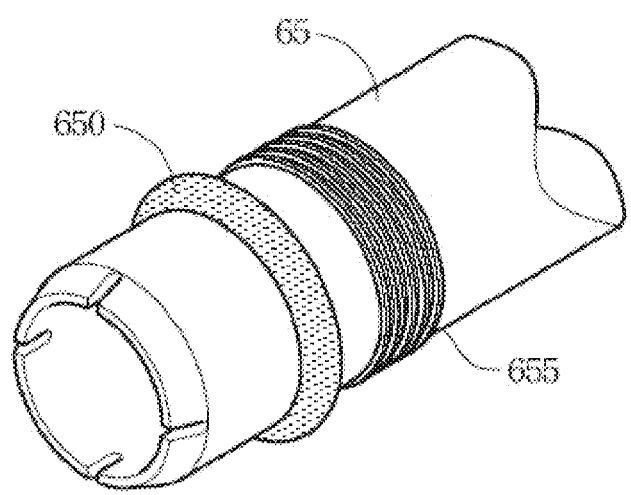
FIG. 12 is a perspective view of a retracting plunger having a rough region in a safety injector according to a sixth embodiment of the present invention.

FIG. 12 describes a sixth embodiment of a safety injector and a plunger combination according to the present invention. In the present embodiment, a rough region 655 constructed from, for example, uneven concave grooves and convex ribs, transverse striatures or rough surface with grains, is provided above a raised portion 650 on an outer surface of a retractable plunger 65. The rough region 655 functions for neutralizing or buffing a user's excessive pushing force acting on the plunger combination so as to prevent the retractable plunger 65 from prematurely retracting into the hollow plunger (not shown) before completion of injection operation so that successful injection can be ensured.

The plunger combination of the automatically retractable safety injector disclosed in the present invention is designed as a two-piece structure. The retractable plunger and the hollow plunger, which are made of a flexible material such as plastic or rubber, are separately molded through injection molding process and then assembled together. Thus, risks of accidentally damaging the plunger during fabrication and failed injection operation caused by the damaged plunger damaged before and during injection operation can be reduced. Besides, since the two-piece plunger can have components thereof separately molded and then assembled, required dimensional precision of molds can be lower than that of the one-piece plunger having the breakable connection wherein mechanical balance of the connected portion thereof has to be taken into consideration. As a result, design and manufacturing costs of the molds are reduced while the reliability and the quality stability of the products are enhanced.

On the other hand, the two-piece plunger combination surpasses the breakable connection used in the plunger of the prior syringe in mechanical balance property for resisting transverse shear. Therefore, when a patient uses his/her single hand to inject himself/herself, or when a medical staff member injects a patient at his/her body portion unfavorable to exerting force, the practicability of the disclosed safety injector and the plunger combination thereof will not be deteriorated because the limitations of force-exerting angle or posture are eliminated.

Figure 13:
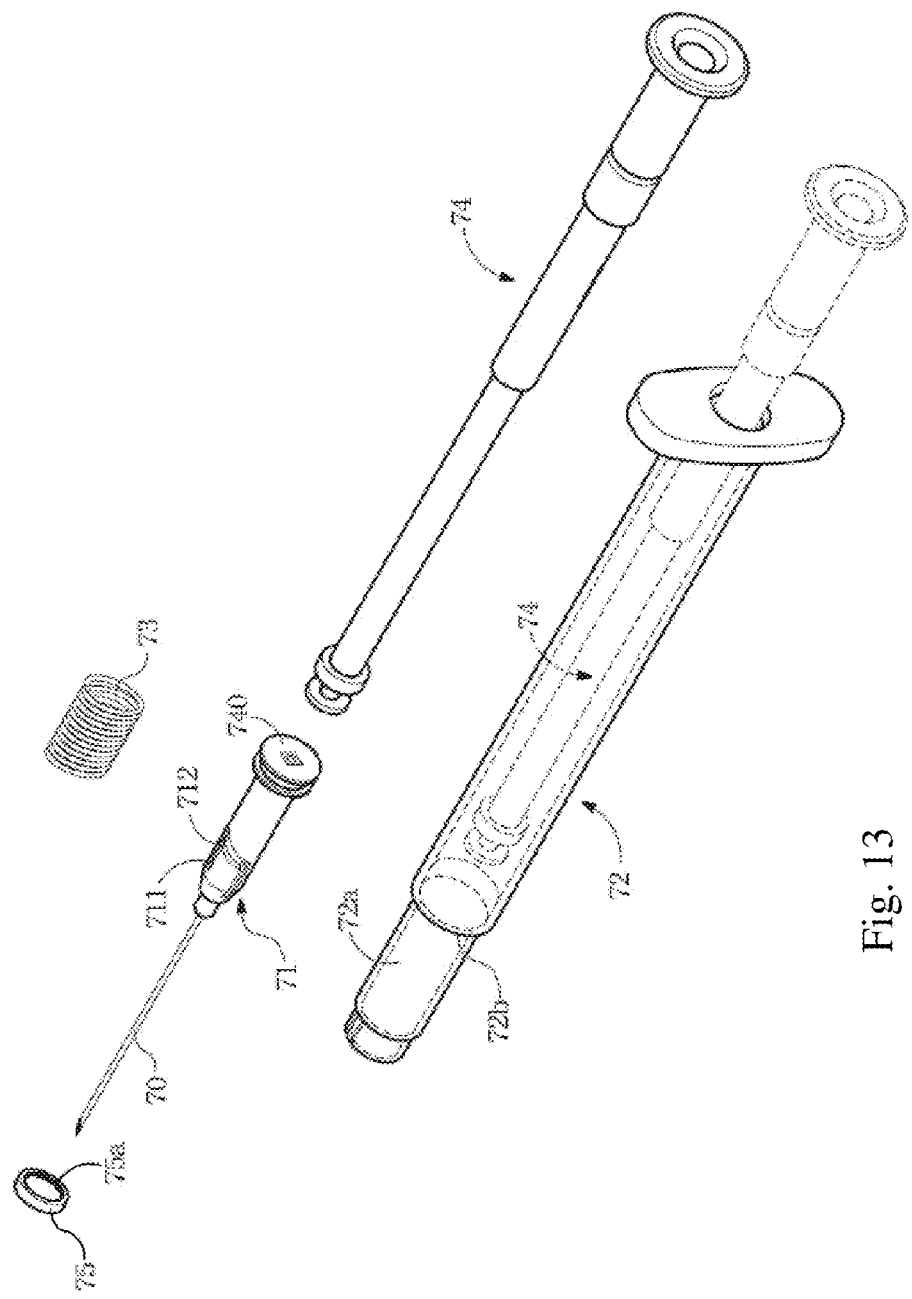
FIG. 13 is an exploded view of a safety injector according to a seventh embodiment of the present invention.

Especially, for improving the yield rate and user practicability of the disclosed safety injector and the plunger combination thereof, an improved design is applied to the needle hub. FIGS. 13 and 14 are provided to illustrate a seventh embodiment and an eighth embodiment of the present invention, respectively.

As shown in FIG. 13, for enhancing retraction of the needle hub, a narrow barrel 72a having a diameter smaller than that of the hollow barrel 72 is integrally formed with the hollow barrel 72 at a front end of the hollow barrel 72 for accommodating a annular retracting spring 73 and a front portion of the needle hub 71. Therein, at least one movable or stable stopper 75 is received around an opening 72b of the hollow barrel 72 where the hollow barrel 72 borders on the narrow barrel 72a, so as to prevent the needle hub 71 from falling off outward when receiving an excessive pushing force during injection operation and to guide the needle hub 71 to retract when injection operation is completed. A through hole 75a is provide at a center of the movable or stable stopper 75 for allowing the needle 70 and part of the needle hub 71 to pass therethrough. Further, the through hole 75a of the stopper 75 has an area smaller than that of a disc 710 of the needle hub 71 so that the needle hub 71 can be retained at a position for the optimum retraction. However, the movable or stable stopper may be one or more rings having an inner wall thereof formed as a smooth surface, or with regular or irregular arranged ratchets. In the present embodiment, a round ring having an inner wall of a through hole thereof formed with radial ratchets is used as a preferable embodying mode. The needle 70, the needle hub 71, positioning grooves 711, U-shaped slide passages 712, and an annular retracting spring 73 are respectively the same as the needle 10, the needle hub 11, the positioning grooves 111, the U-shaped slide passage 112, and the annular retracting spring 13 described in the first embodiment.

Figure 14A:
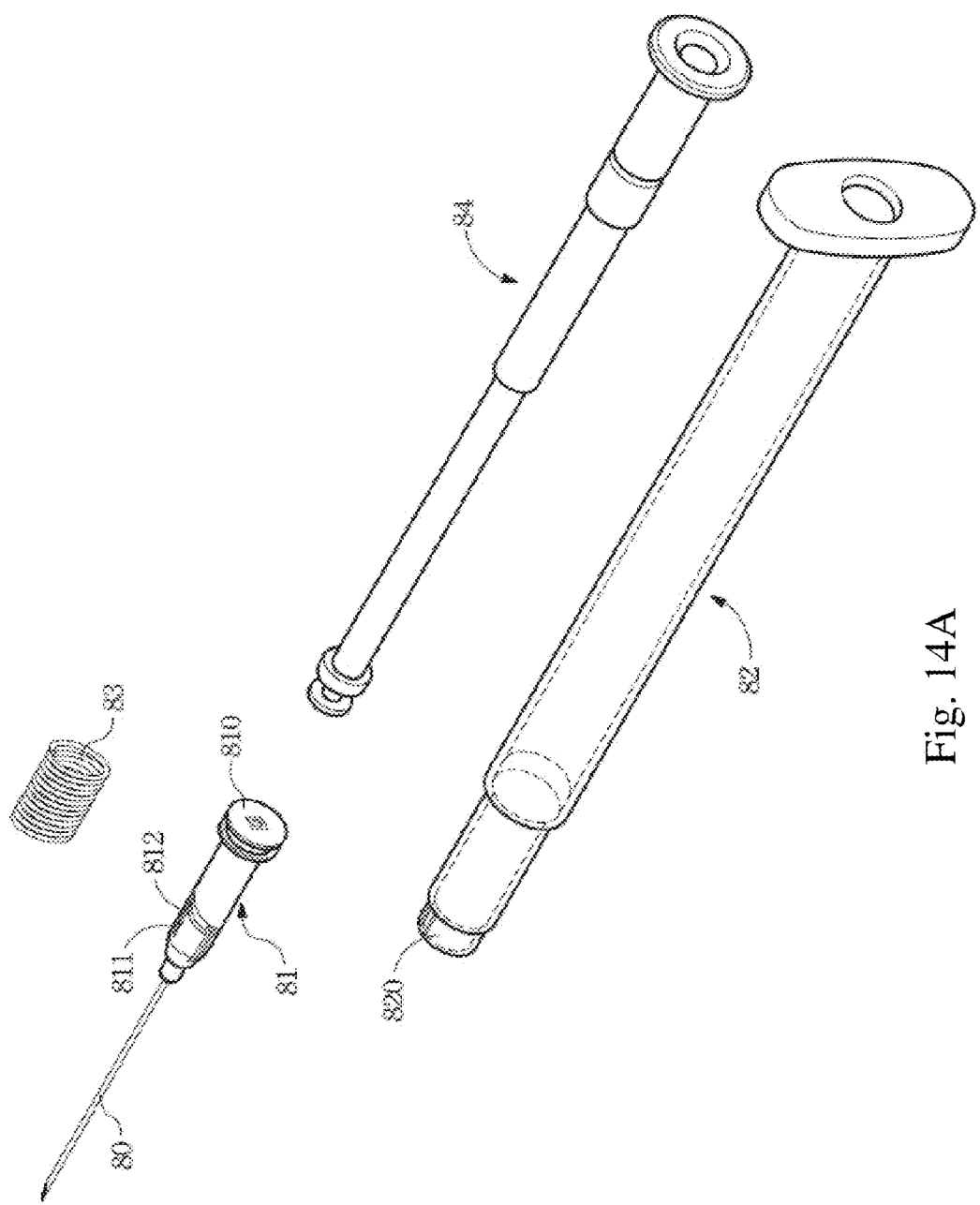
FIGS. 14A and 14B are an exploded view and a partial cross sectional view of a safety injector according to an eighth embodiment of the present invention.
Figure 14B:
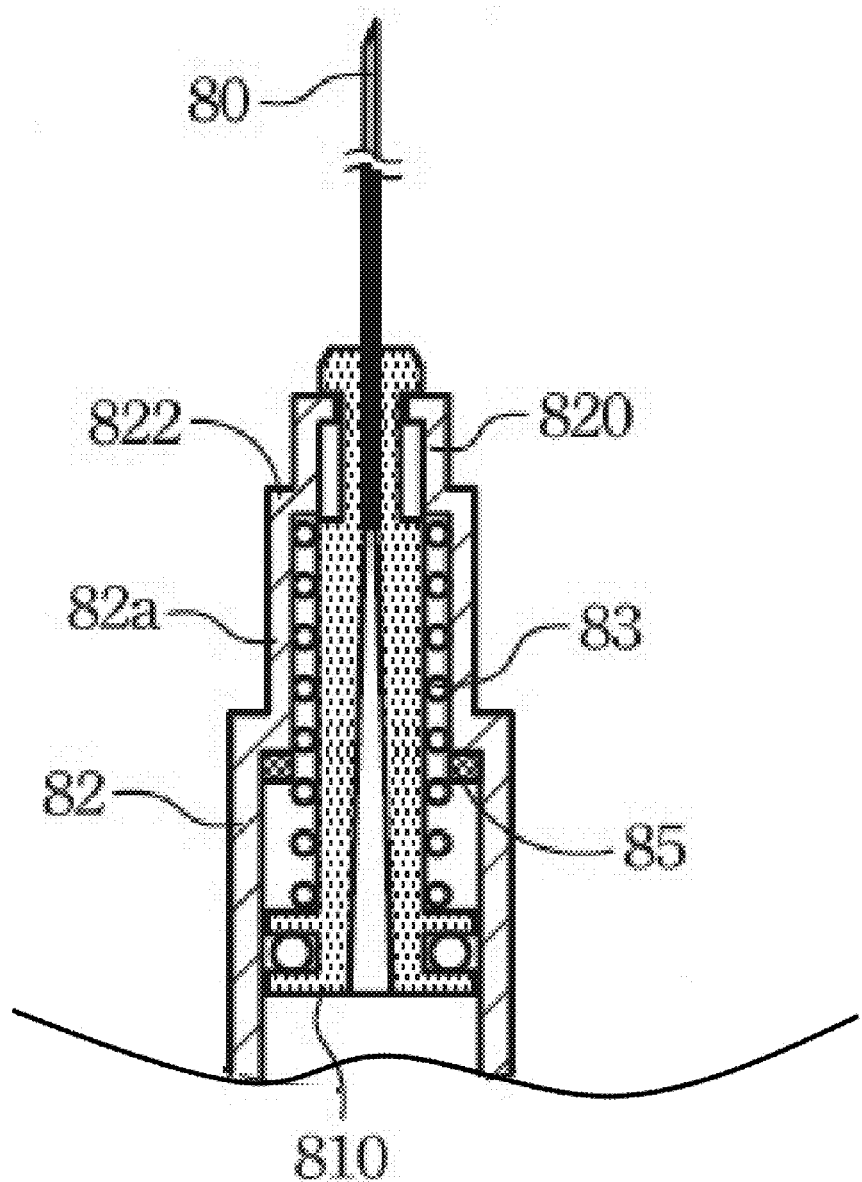

Besides, in the eighth embodiment, the present also discloses a neck portion 85 formed integrally with an opening of the hollow barrel 82 where the hollow barrel 82 borders on the narrow barrel 82a while the hollow barrel 82 is molded through injection molding process, as shown in FIG. 14A and FIG. 14B, in addition to the movable or stable stopper 75 formed at the opening 72b of the narrow barrel 72a. A through hole is provide at a center of the neck portion 85, which has an area smaller than that of a disc 810, so that the disc 810 can be retained by the neck portion 85 and only allow a needle 80 and a front portion of a needle hub 81 to pass therethrough. Thereupon, the needle hub 81 can be also prevented from falling off outward. A plunger combination 84, an annular retracting spring 83, positioning grooves 811, U-shaped slide passages 812, and an elastic retaining hook 822 are respectively the same as the plunger combination 14, the annular retracting spring 13, the positioning grooves 111, the U-shaped slide passage 112, and the elastic retaining hook 122 described in the first embodiment.

The present invention also discloses a ninth embodiment. The safety injector of this embodiment is suitable for injecting non-liquid materials for medical or non-medical purpose, such as injecting solid drugs for administrating subcutaneously, implantable biological chips, or gel-like medicine.

Figure 15:
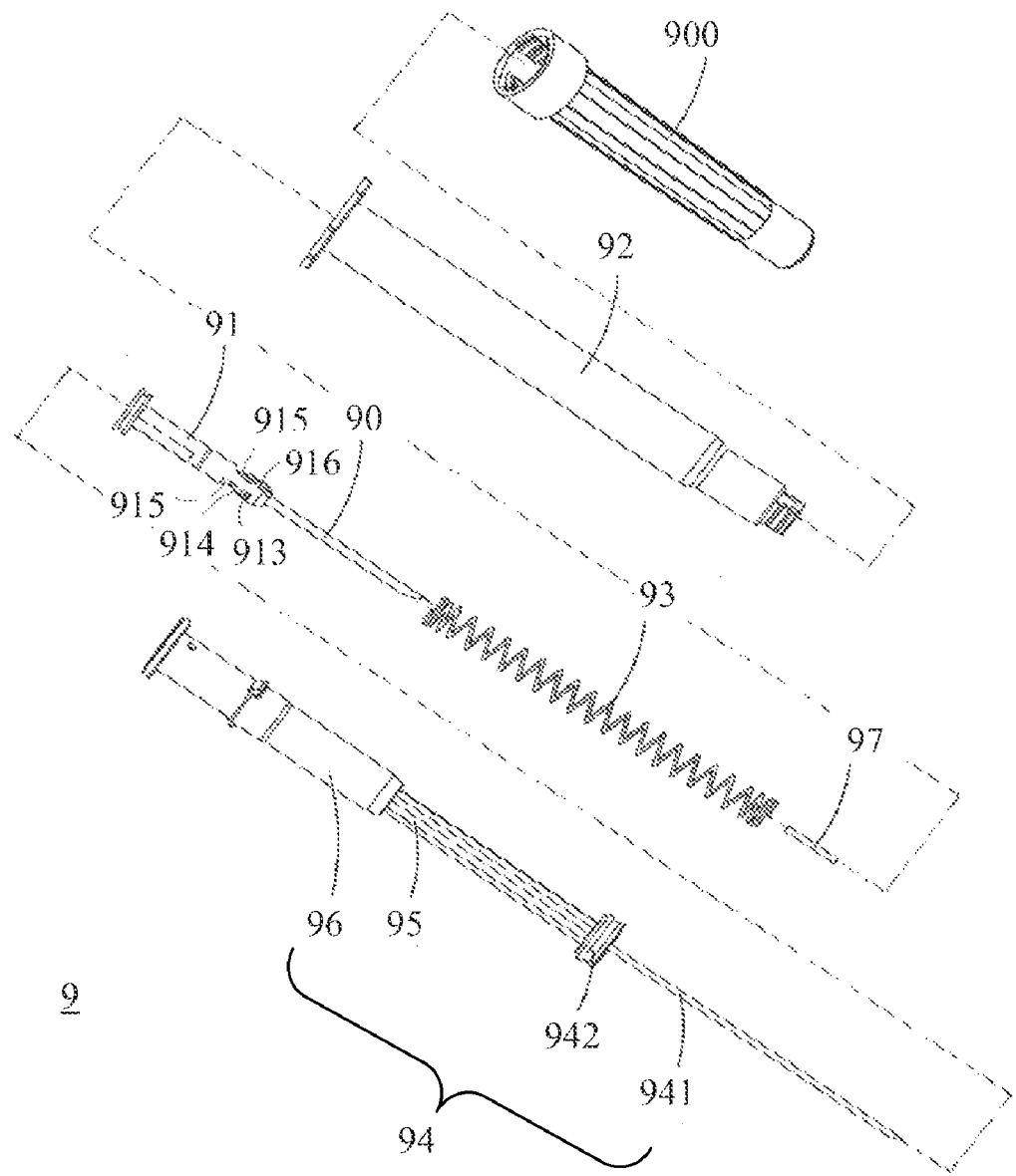
FIG. 15 is an exploded view of a safety injector according to an ninth embodiment of the present invention.

Please refer to FIG. 15. The safety injector 9 comprises a cap 900, a needle hub 91 connecting a needle 90, a hollow barrel 92 connecting the needle hub 91, a collapsable plunger combination 94 settled in the hollow barrel 92. The collapsable plunger combination 94 comprises a rod 941, retractable plunger 95 and a hollow plunger 96. The retratable plunger 94 further comprises a plunger head 942. The rod 941 extends from one end (i.e., the plunger head 942) of the retractable plunger 95 and toward the needle hub 91.

Figure 16:
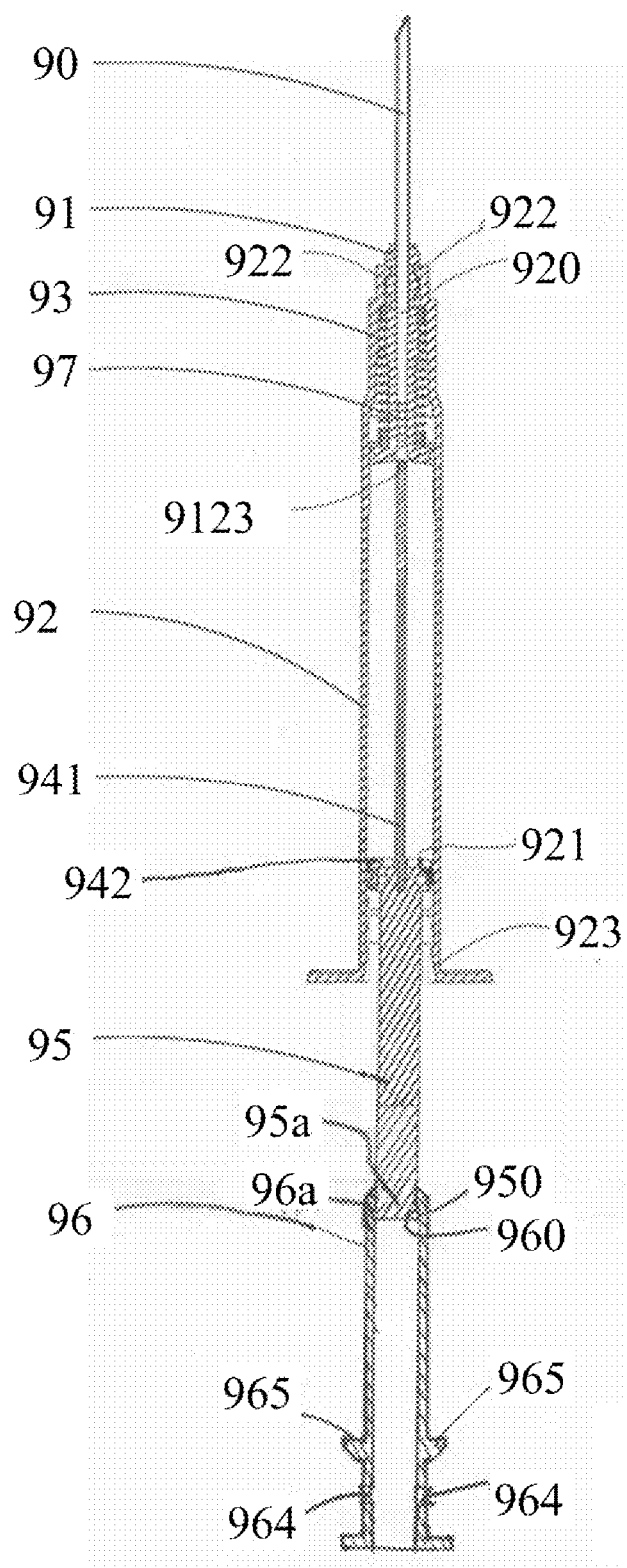
FIG. 16 is a cross sectional view of a safety injector according to the ninth embodiment of the present invention.

Please refer to FIG. 16. The collapsable plunger combination 94 is settled in the hollow barrel 92. The hollow barrel 92 engages with the needle hub 91 and at least one annular retracting spring 93 is implemented to guide the needle hub 91 to retract along a direction opposite to a direction where the needle hub 91 moves during the injection. The hollow barrel 92 connecting the needle hub 91 can guide the needle hub 91 to retract into the hollow barrel 92 after an injection is completed. The safety injector 9 preferably further comprises a protrusion 921 disposed on an inner wall of the hollow barrel 92 distant from the needle 90. The protrusion 921 can provide an interfering force for the plunger head 942 to engage with the protrusion 921 when the safety injector 9 is assembled and during shipping. Accordingly, the collapsable plunger combination 94 will not easily being pushed into the hollow barrel 92 so as to avoid the injectant 97 to be wrongfully injected into the patient.

Figure 17:
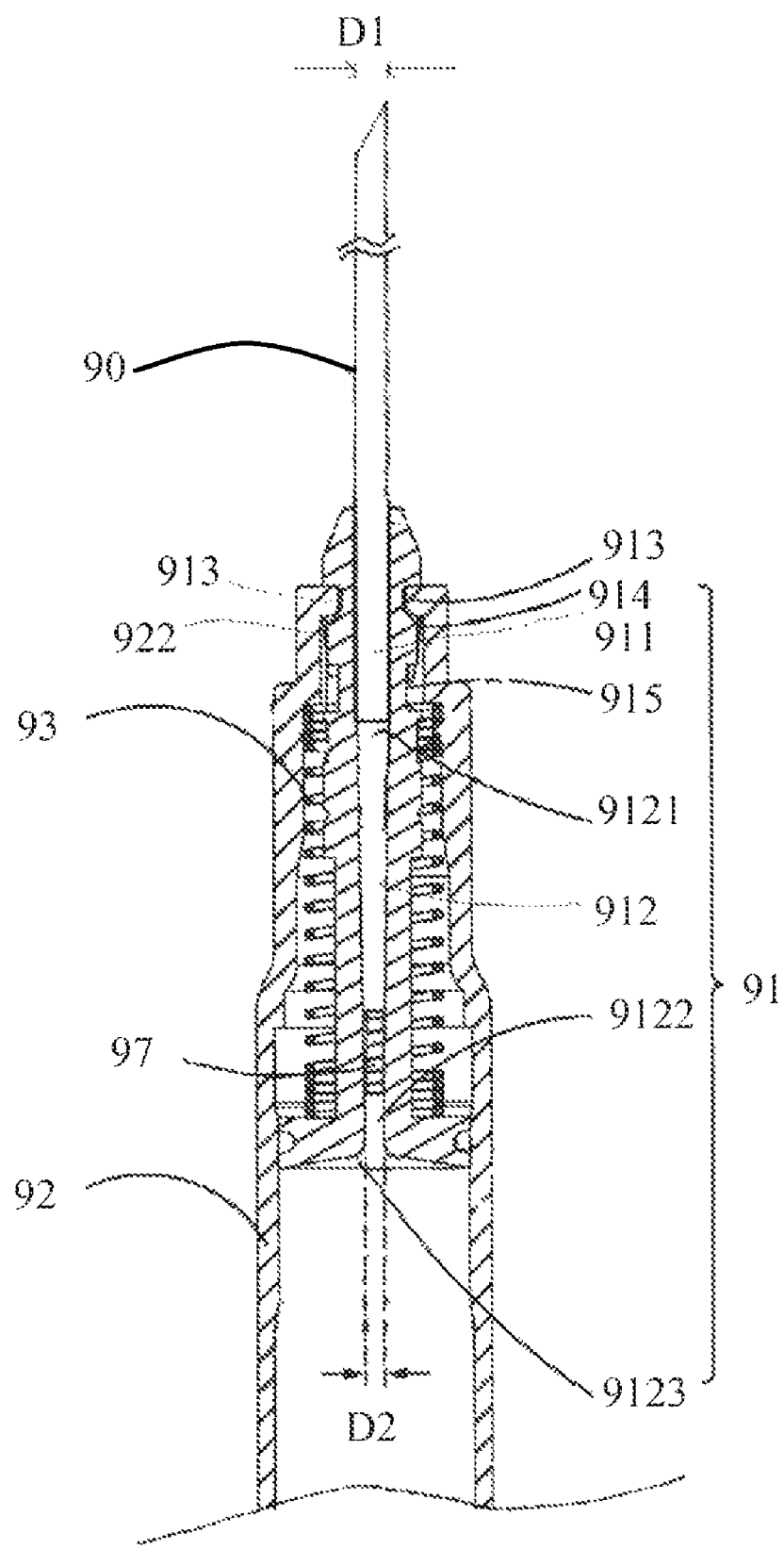
FIG. 17 is a partial cross sectional view of the needle hub and hollow barrel of the safety injector according to the ninth embodiment of the present invention.

Please refer to FIG. 17. The needle hub 91 comprises an insertion portion 911 therein and a hollow track 912 connecting with the insertion portion 911. The insertion portion 911 is for accommodating the needle 90. The hollow tract 912 further comprises a distal end 9121 and a proximal end 9122. The distal end 9121 of the hollow tract 912 has a first inner diameter D1 and the proximal end 9122 has a second diameter D2 and the first inner diameter D1 is larger than the second inner diameter D2. In addition, the bottom of the needle hub 91 preferably further comprises an incline configuration 9123 so that the rod 941 is more easily guided and inserted into the hollow tract 912 where the injectant 97 is placed when the injection is initiated.

Furthermore, the hollow barrel 92 has the front end 920 and a rear end 923. A plurality of elastic retaining hook 922, which are slightly flexible, are disposed at the front end 920 of the hollow barrel 92 in a manner that the elastic retaining hooks 922 face a center of the hollow barrel 92. In addition, the needle hub 91 further comprising a plurality of slots 913, slopes 914, turning chutes 915 and guiding chutes 916 (shown in FIG. 15). The slots 913, slopes 914, the turning chutes 915, and the guiding chutes 916 are connected in series. When the disclosed subject matter is in an original state before being used and during injection operation, the retaining hooks 922 of the hollow barrel 92 engage with the slots 913 to clamp the needle hub 91. When the user continuously presses on the hollow plunger 96 after the injection is completed, the retaining hooks 922 will be indirectly pressed and flexibly expanded so that the retaining hooks 922 disengage with the slots 913. After detaching from the slots 913, the retaining hooks 922 will slide along the slopes 914, the turning chutes 915, and the guiding chutes 916. The annular retracting spring 93 is further pressed when the retaining hooks 922 slides to the turning chute 915. When the retaining hooks 922 slides to the guiding chutes 916, the annular retracting spring 93 starts to relax. Accordingly, the needle hub 91 will be guided and pushed by the annular retracting spring 93, and then will be retracted into the hollow barrel 92.

Figure 18:
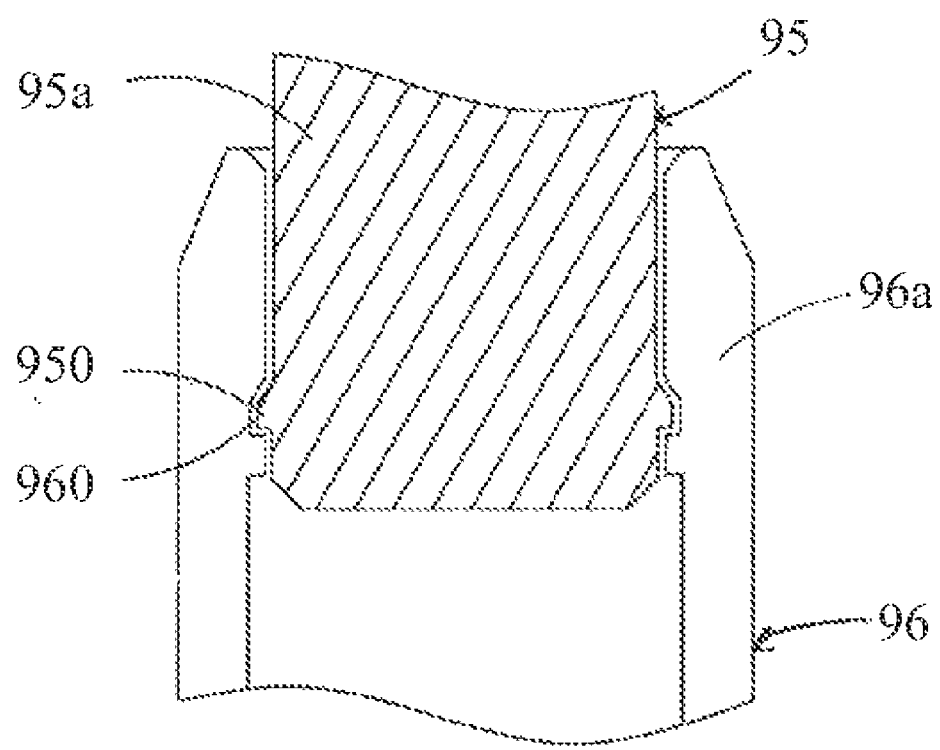
FIG. 18 is a partial cross sectional view of the telescoping portion of the plunger combination of the safety injector according to the ninth embodiment of the present invention.

Please now refer to FIG. 18. The hollow plunger 96 comprises a first telescoping part 96a and the retractable plunger 95 comprises a second telescoping part 95a. The first telescoping part 96a telescopes with the second telescoping part 95a, and at least one raised portion 950 formed on an outside wall of the second telescoping part 95a to be correspondingly embedded in at least one depression 960 formed on an inside wall of the first telescoping part 96a. The raised portion 950 and the depression 960 engage to each other.

Figure 19A:
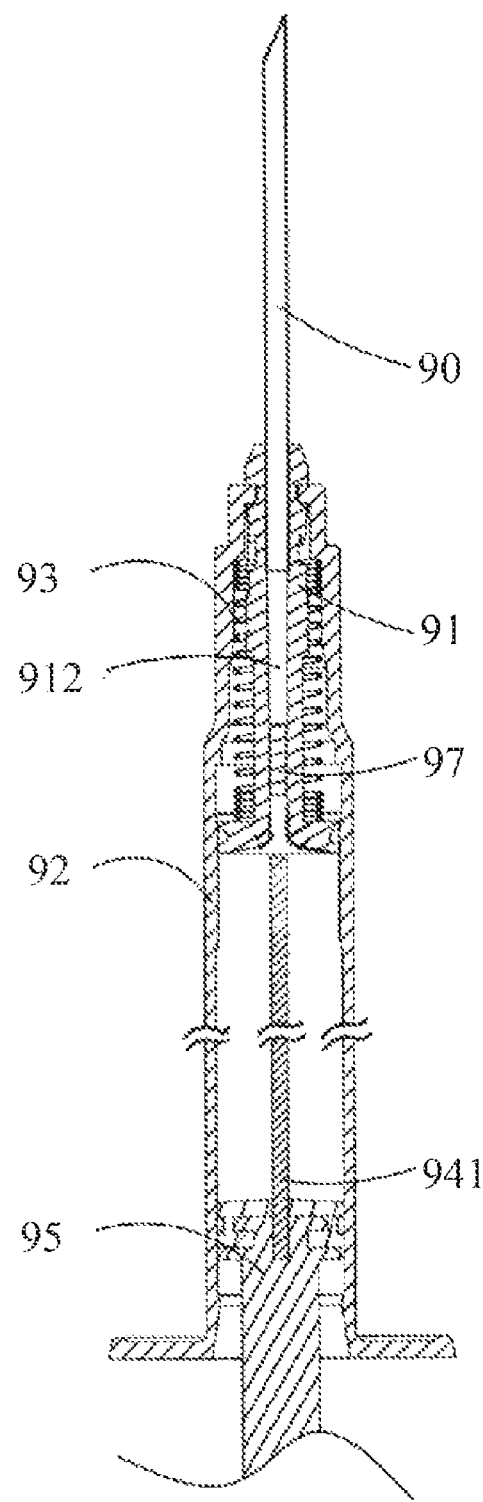
FIG. 19A is a partial cross sectional view of the safety injector according to the ninth embodiment of the present invention to show the pushing of an injectant.
Figure 19B:
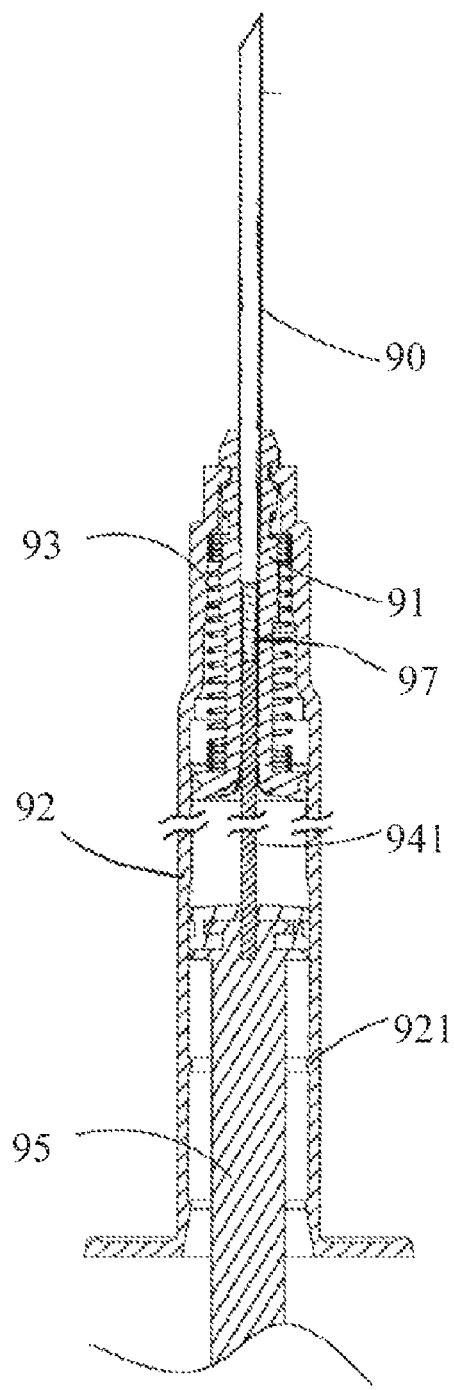
FIG. 19B is a partial cross sectional view of the safety injector according to the ninth embodiment of the present invention to show the pushing of an injectant.
Figure 19C:
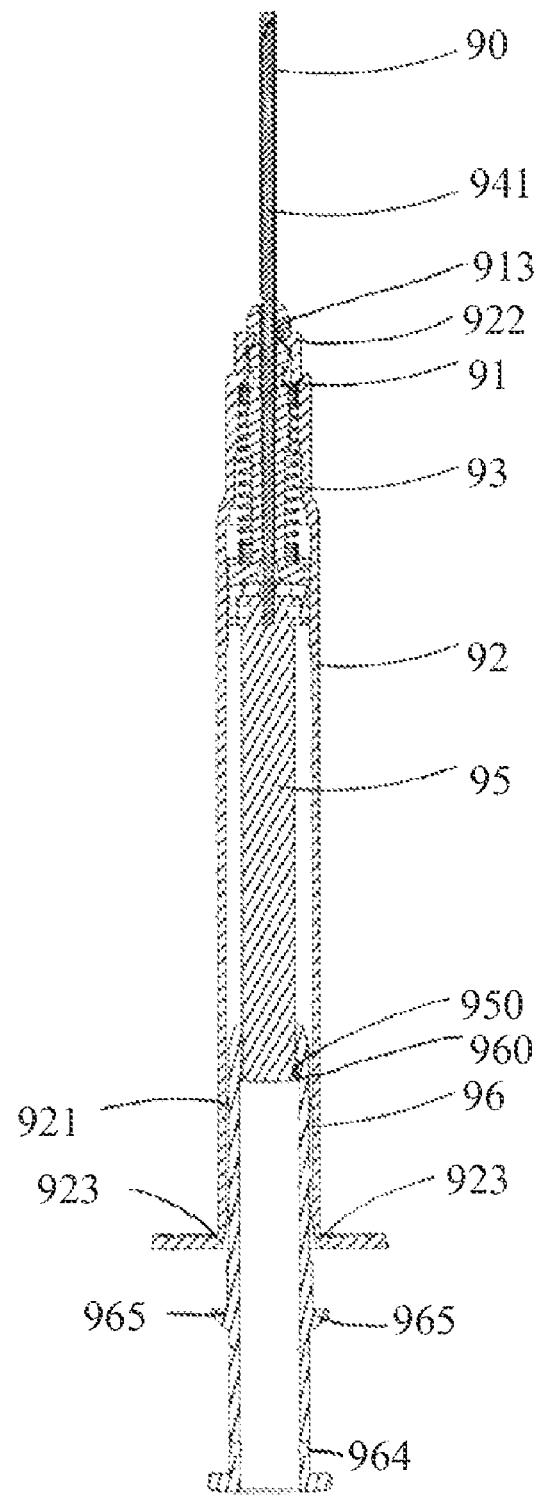
FIG. 19C is a cross sectional view of the safety injector according to the ninth embodiment of the present invention to show the completion of the injection.

Please now refer to FIGS. 19A, 19B, 19C, 19D, 19E, and 19F. As shown in FIGS. 19A and 19B, during injecting, the rod 941 pushes the injectant 97 (either solid or gel-like) from the hollow tract 912 into the needle 90. Eventually, the injectant 97 is injected into the body of a patient through the needle 90. FIG. 19C represents the safety injector 9 after the injection is complete and before the retraction of the needle 90, the needle hub 91 and the retractable plunger 95 is initiated.

Figure 19D:
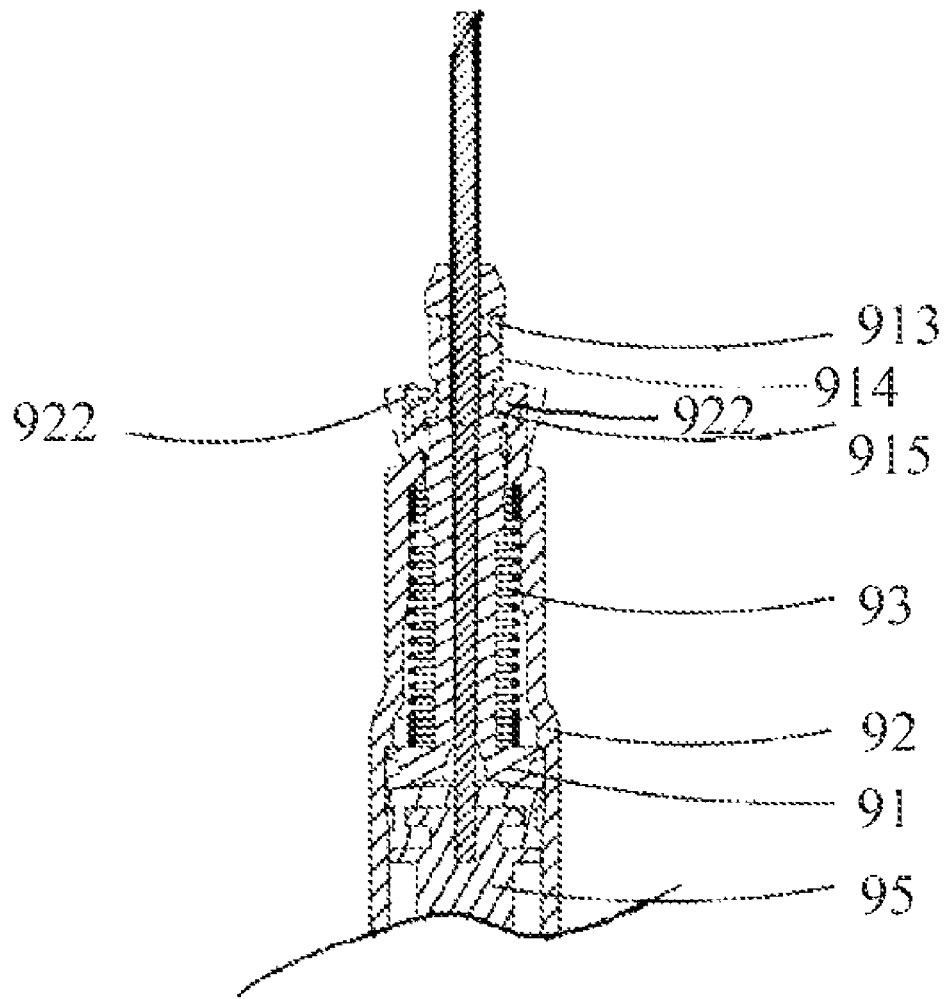
FIG. 19D is a cross sectional view of the safety injector according to the ninth embodiment of the present invention to show the retraction of the needle hub.

In addition, as described previously, the retaining hooks 922 will be indirectly pressed and flexibly expanded so that the retaining hooks 922 disengage with the slots 913. After detaching from the slots 911, the retaining hooks 922 will slide along the slopes 914, the turning chutes 915, and the guiding chutes 916, so that the needle hub 91 will be guided and retracted into the hollow barrel 92. As shown in FIG. 19D, the retaining hooks is flexibly expanded and now slides into the turning chute 915.

Figure 19E:
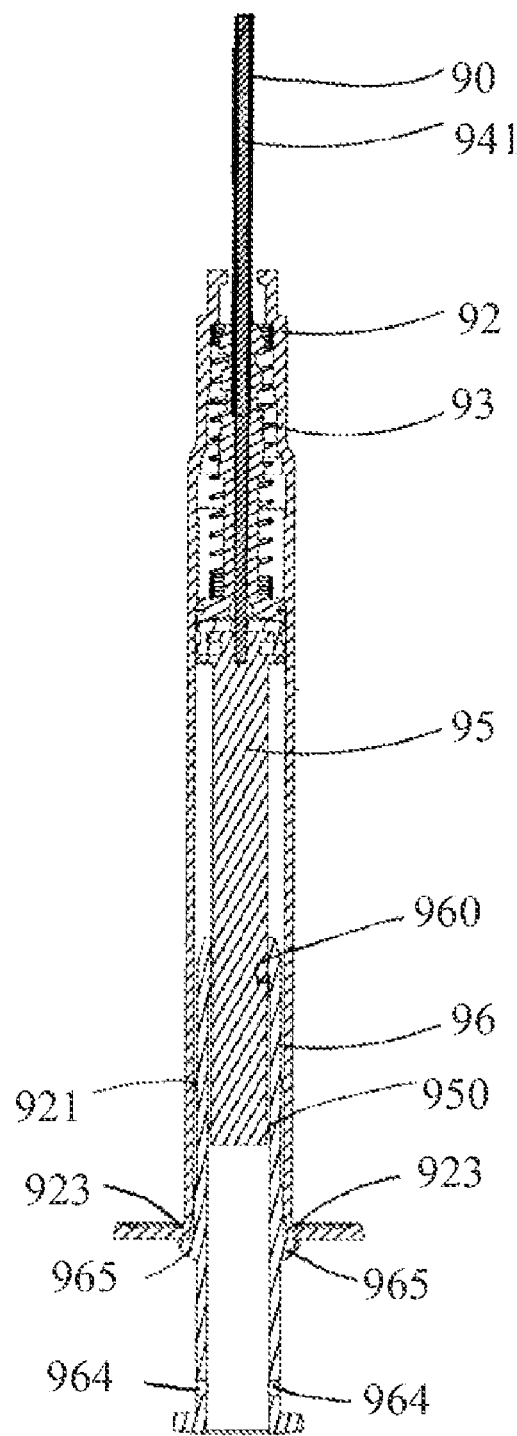
FIG. 19E is a cross sectional view of the safety injector according to the ninth embodiment of the present invention to show the retraction of the retractable plunger and the needle hub.
Figure 19F:
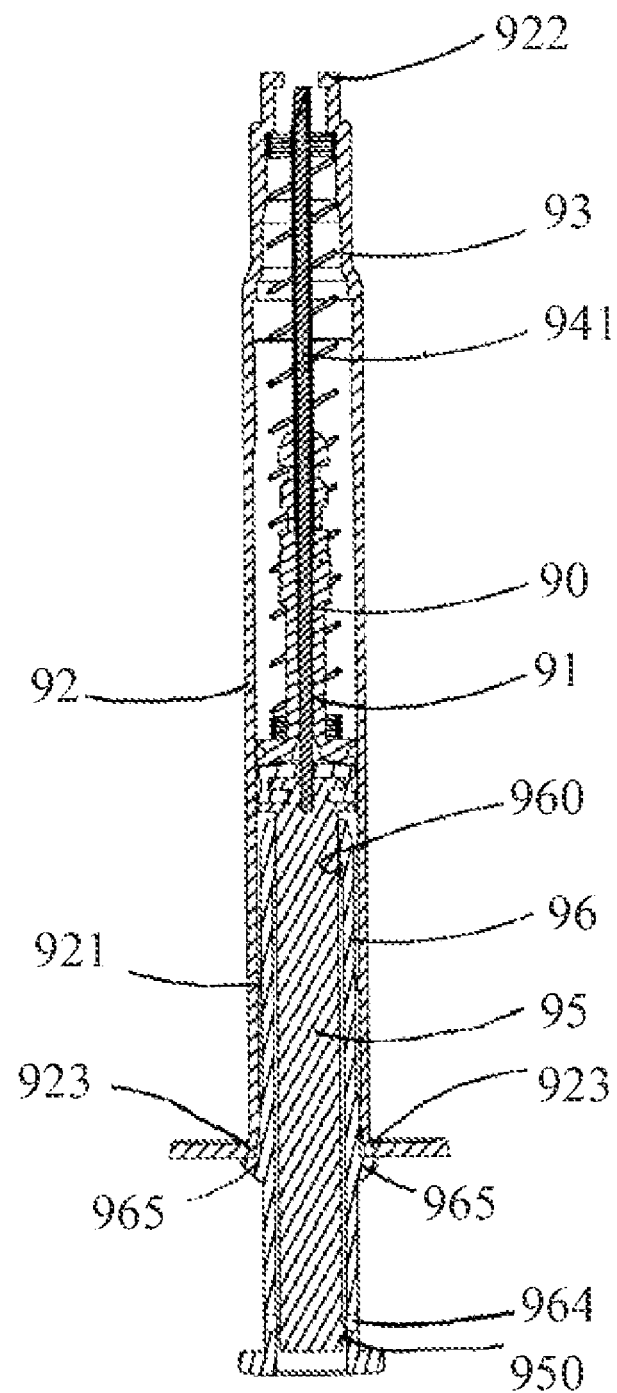
FIG. 19F is a cross sectional view of the safety injector according to the ninth embodiment of the present invention to show the completion of the retraction of the retractable plunger and the needle hub.

As shown in FIG. 19E, after the injection is completed, the engagement between the raised portion 950 and the depression 960 is released to make the retractable plunger 95 retract into the hollow plunger 96 when a following press on the hollow plunger 96. Therefore, a space in the hollow barrel 92 originally occupied by the retractable plunger 95 can be spared for accommodating the retracted needle hub 91. As shown in FIG. 19F, eventually, the needle 90, the needle hub 91, and the rod 94 is retracted into the hollow barrel 92.

Furthermore, as shown in FIGS. 19C, 19E, and 19F, two stoppers 965 are formed on the two outer lateral wall of the hollow plunger 96 and positioned distant from the first telescoping portion 96a. After the injection is completed, the stoppers 965 engages with the rear end 923 of the hollow barrel 92 and contribute to prevent the hollow plunger 96 to be further pushed into the hollow barrel 92.

Figure 20A:
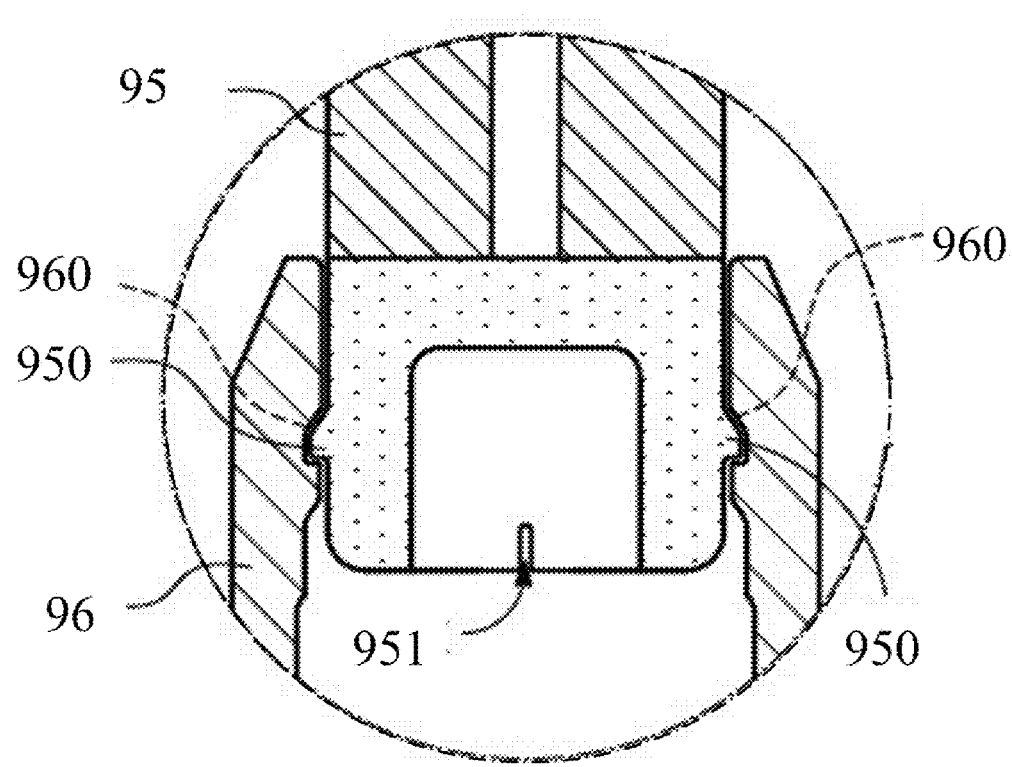
FIG. 20A is a schematic drawing of the retracting plunger and the hollow plunger according to the ninth embodiment of the present invention.
Figure 20B:
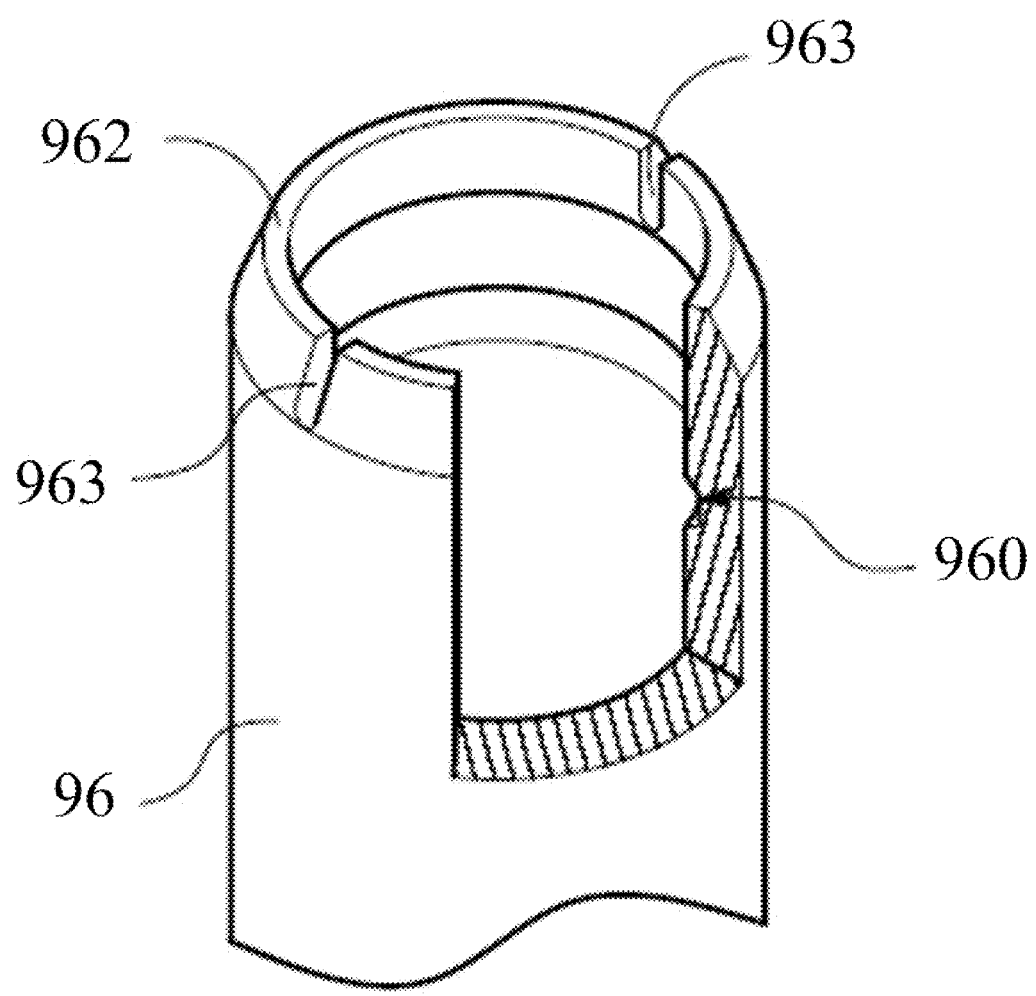
FIG. 20B is a schematic drawing of the hollow plunger according to the ninth embodiment of the present invention.

Please refer to FIG. 20A, in order to maintain balancing of stresses on the plunger combination 94, the present embodiment also provides a modified mode. One or more transverse stress adjustable notches 951 are optionally disposed on the second telescoping part 95a and positioned at a center of the retractable plunger 95. The transverse stress adjustable notches 951 may be caves, blind holes or through holes. Generally, each of the transverse stress adjustable notches 951 has a lengthwise depth not approaching or reaching a position where the raised portions 950 are formed on the outer surface of the retractable plunger 95. Thereupon, when the plunger combination 94 is continuously pushed after completion of injection operation, the transverse stress adjustable notches 951 can become deformed so as to make the raised portions 950 detach from the depressions 960. In addition, as shown in FIG. 20B, at least one stress adjustable notch 961 can be also optionally disposed on the inclined upper edge 962 of the hollow plunger 96. The stress adjustable notch 961 has a lengthwise depth not reaching the depressions 960 on the inner surface of the hollow plunger 96 and may be, for example, a cave or a blind hole.

More detailed, the needle hub 91 further comprising a plurality of slots 911, slopes 912, turning chutes 913 and guiding chutes 914. The slots 911, slopes 912, the turning chutes 913, and the guiding 914 are connected in series. The retaining hooks 922 of the hollow barrel 92 engage with the slots 911 to clamp the needle hub 91. When the user continuously presses on the hollow plunger after the injection is completed, the retaining hooks 922 disengage with the slots 911. After detaching from the slots 911, the retaining hooks 922 slide along the slopes 912, the turning chutes 913, and the guiding chutes 913, so that the needle hub 91 is guided and retracted into the hollow barrel 92.

As shown in FIG. 17, the hollow plunger 96 of the plunger combination 94 is provided with one or more exhausting opening 964 formed on a lateral wall of the hollow plunger 96 and positioned distant from the first telescoping part 96a. Thereupon, when the retractable plunger 95 retracts into the hollow plunger 96, air resistance can be eliminated through the exhausting opening 964 and does not hinder pushing operation of a user's thumb so as to facilitate the user's operation.

Furthermore, as shown in FIG. 16, two stoppers 965 are formed on the two outer lateral wall of the hollow plunger 96 and positioned distant from the first telescoping portion 96a. The stoppers 965 contribute to prevent the hollow plunger 96 to be further pushed into the hollow barrel 92 after the injection is complete.

Furthermore, the raised portions 950 in the present embodiment may be a plurality of raised dots integrally formed on the retractable plunger 95 when the retractable plunger 95 is molded through injection molding process. Shapes, dimensions, amounts and arrangement of the raised dots are not to be limited by the present embodiment. However, in the present embodiment, six dots symmetrically arranged are implemented as a preferable embodying mode while a plurality of adjacent rows of convex annular ribs may be also used as equivalent substitutes of the raised portions 950 described in the present embodiment.

The structure of the hollow plunger 96 is substantially the same as that of the hollow plunger 16 (shown in FIG. 4) described previously in the first embodiment. To make the hollow plunger 96 partially telescope and firmly engage with the retractable plunger 95, the plurality of depressions 960 are formed on the inner wall of the hollow plunger 96 near where the hollow plunger 96 partially telescopes the retractable plunger 95 for engaging the plurality of raised portions 950. The depressions 960 may be recesses, dents or partial or intact concave annular ribs and the depressions 960 may have C-shaped, chamfered rectangular, or irregular sectional shapes. Actually, depressions having any sectional shapes may be equivalent substitutes of the depressions 960 of the present embodiment, as long as the sectional shapes thereof can firmly engage with the raised portions 950 of the retractable plunger 95.

Figure 21A:
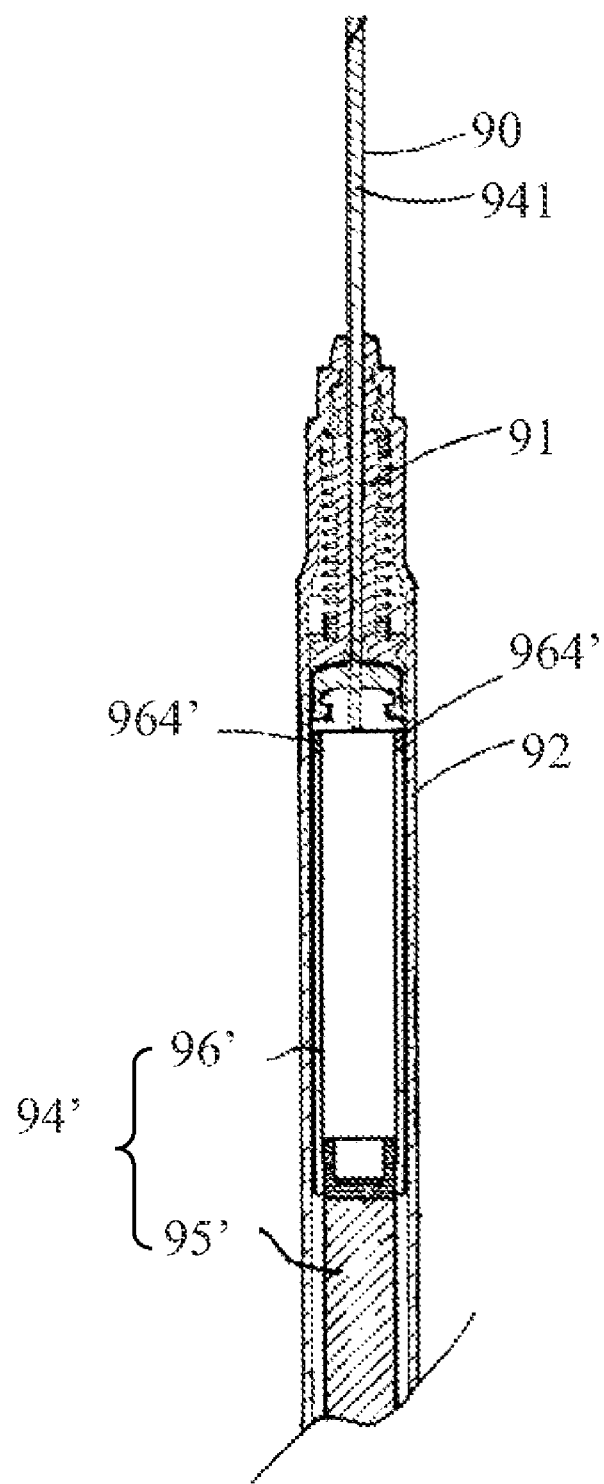
FIG. 21A is an alternative embodying mode of the safety injector according to the ninth embodiment of the present invention.
Figure 21B:
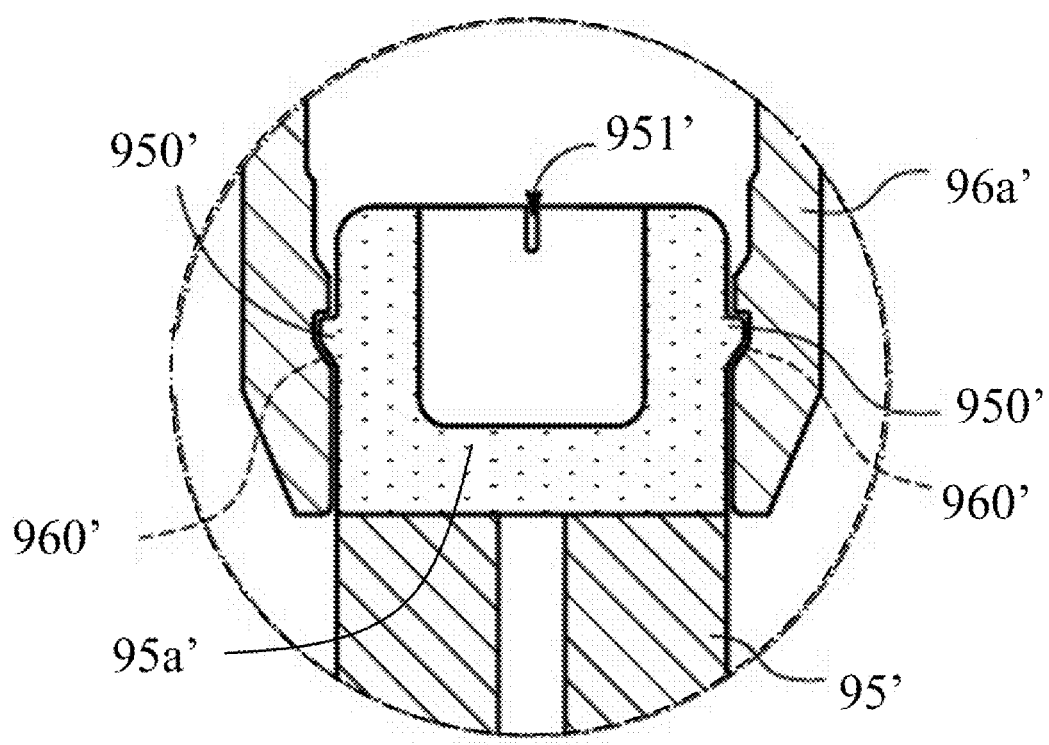
FIG. 21B is an alternative embodying mode of the safety injector according to the ninth embodiment of the present invention.

Now please refer to FIG. 21A to 21D. A plunger combination 94' is a two-piece combination composed of a retractable plunger 95' and a hollow plunger 96'. As shown in FIG. 21B, a plurality of raised portions 950' are formed an outer surface of the second telescoping part 95a' of the retractable plunger 95' while a plurality of depressions 960' are formed on an inner surface of the first telescoping part 96a' of the hollow plunger 96' positionally corresponding to the raised portions 950'. When the plunger combination 94' is in an original state before being used or during injection operation, the raised portions 950' of the retractable plunger 95' firmly engage with the depressions 960' of the hollow plunger 96'.

The safety injector 9 of this embodying mode also further comprises at least one exhausting opening 964' disposed on the hollow plunger 96' and positioned distant from the first telescoping part 96a'.

The difference between the present embodying mode and the aforesaid embodying mode is that the retractable plunger 95' and the hollow plunger 96' are positionally exchanged. The rod 94' extends from one end of the hollow plunger 96' and toward the needle hub 91'. When a user continuously pushes the plunger combination 94' toward the needle 90 after completion of injection operation, the raised portions 950' formed on a top portion of the inner wall of the retractable plunger 95' are forced to detach from the depressions 960' so that the retractable plunger 95' can retract into the hollow plunger 96'.

Figure 21C:
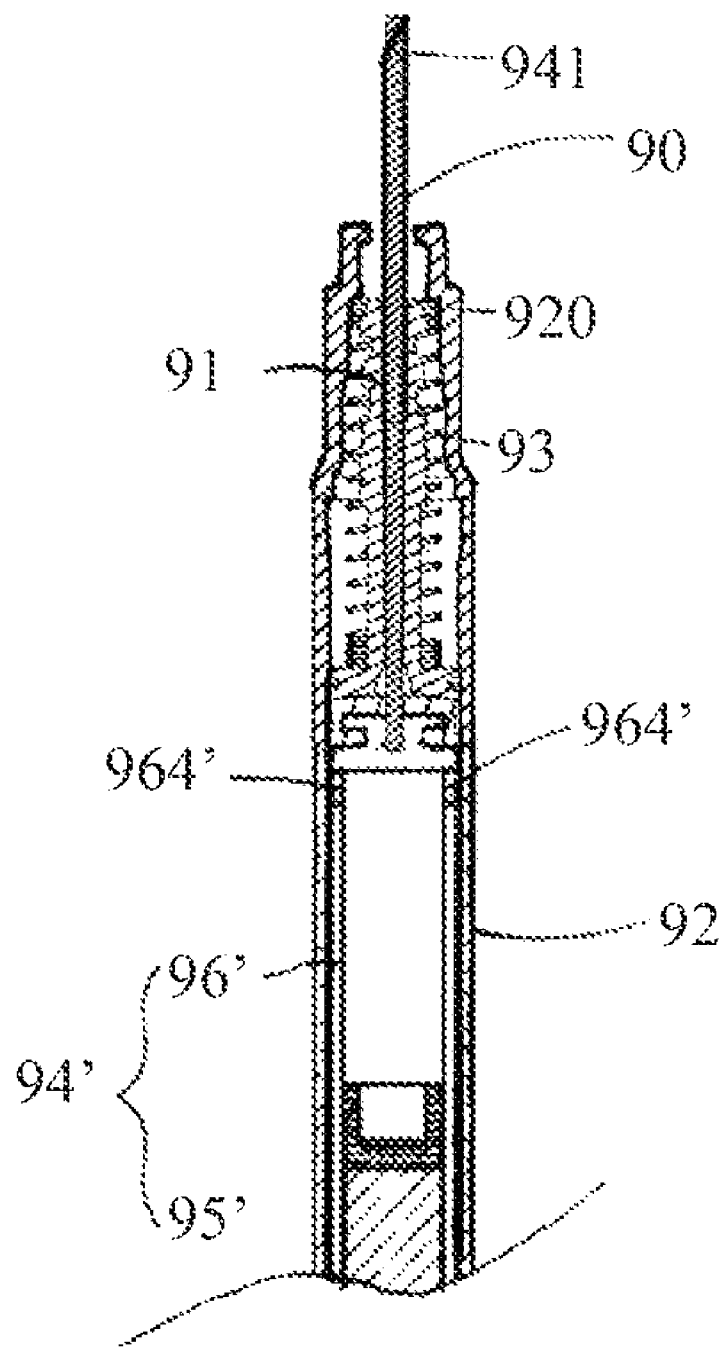
FIG. 21C is an alternative embodying mode of the safety injector according to the ninth embodiment of the present invention.
Figure 21D:
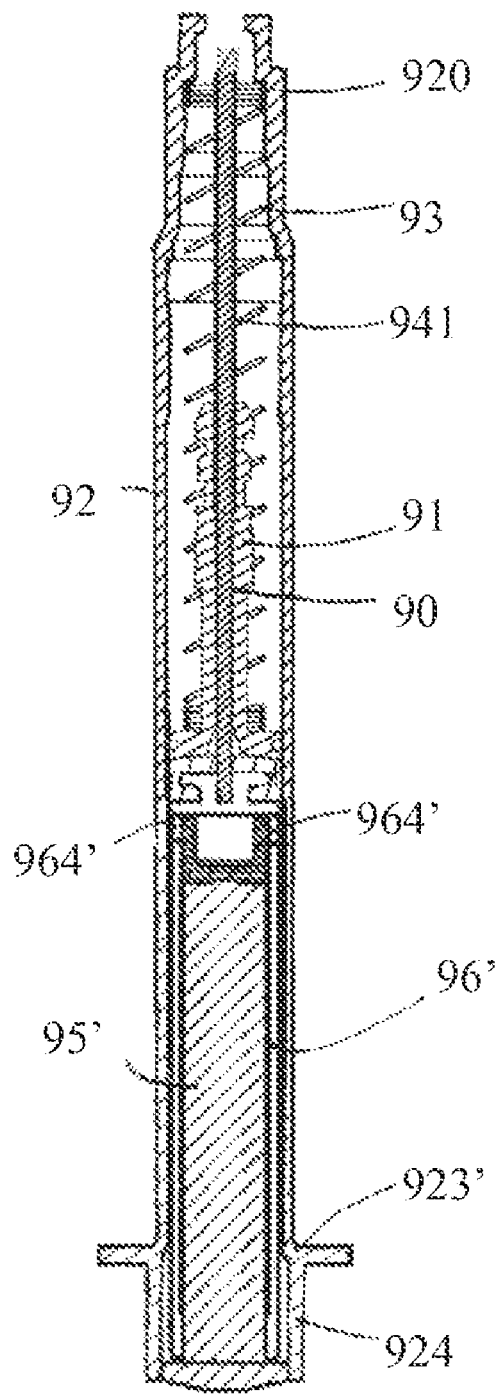
FIG. 21D is an alternative embodying mode of the safety injector according to the ninth embodiment of the present invention to show the completion of the retraction.

At this time, as shown in FIGS. 21C and 21D, a direction where the retractable plunger 95' retracts into the hollow plunger 96' is opposite to a direction where the needle hub 91 retracts into the hollow barrel 92 after the raised portions 950' detach from the depressions 960'. Even, to ensure the preferable practicability for one-hand operation of the plunger combination 94' having the retractable plunger 95' positioned at the rear end 923 of the hollow barrel 92, a wing 924 may be provided at the rear end 923 of the hollow barrel 92. And the bottom of the retractable plunger 95' is stopped to prevent the retractable plunger 95' from further entering into the hollow barrel 92, and thereby to control the distance which the retractable plunger 95' enters into the hollow barrel 92, so as to spare a sufficient space in the hollow barrel 92 for accommodating the needle hub 91.

All the details described above are preferable embodying modes of the first embodiment of the present invention and not to be regarded as limitations to the present invention. Any plunger combination is a two-piece combination composed of a hollow plunger and a retractable plunger that are partially telescoped shall be considered as within the equivalent range of the present invention despite the modifications on sequence, combining means and segmental connection of the hollow plunger and the retractable plunger. Meanwhile, the present invention further provides a reinforcing design for the retractable plunger and the hollow plunger of the plunger combination for harmonizing with force strength of one-hand operation and various force-exerting angles.

Although some particular embodiments of the invention have been described in detail for purposes of illustration, it will be understood by one of ordinary skill in the art that numerous variations will be possible to the disclosed embodiments without going outside the scope of the invention as disclosed in the claims.

What is claimed is:
1. A safety injector comprising:
a needle hub connecting a needle, the needle hub comprising a inserting part therein and a hollow track connecting with the inserting part, the inserting part being for accommodating the needle and the hollow tract further comprising a distal end and a proximal end, the distal end of the hollow tract having a first inner diameter and the proximal end having a second diameter, and the first inner diameter being larger than the second inner diameter, wherein the needle hub further comprises a plurality of slots, slopes, turning chutes and guiding chutes connected serially;
a hollow barrel connecting the needle hub for guiding the needle hub to retract into the hollow barrel after an injection is completed, wherein the hollow barrel comprises a plurality of hooks, the plurality of hooks engage with the slots to clamp the needle hub; and
a collapsable plunger combination settled in the hollow barrel, the collapsable plunger combination comprising a rod, a retractable plunger and hollow plunger, the rod extending from one end of the retractable plunger toward the needle hub, the hollow plunger comprising a first telescoping part and the retractable plunger comprising a second telescoping part, the first telescoping part telescoping with the second telescoping part, there being at least one raised portion formed on an outside wall of the second telescoping part to be correspondingly embedded in at least one depression formed on an inside wall of the first telescoping part, the raised portion and the depression engaging to each other;
wherein the engagement between the raised portion and the depression is released to make the retractable plunger retract into the hollow plunger when a following press on the hollow plunger after an injection is completed, and thereby spare a space of the hollow barrel for accommodating the needle hub, and when the following press is applied on the hollow plunger after the injection is completed, the hooks of the hollow barrel disengage with the slots and slide along the slopes, the turning chutes, and the guiding chutes, so that the needle hub is guided and retracted into the hollow barrel.
2. The safety injector of claim 1, further comprising at least one stress adjustable notch disposed on first telescoping part.

3. The safety injector of claim 1, further comprising at least one stress adjustable notch disposed on second telescoping part.

4. The safety injector of claim 1, wherein the bottom of the needle hub further comprises an incline configuration.

5. The safety injector of claim 1, further comprising a protrusion disposed on an inner wall of the hollow barrel and being distant from the needle.

6. The safety injector of claim 1, further comprising at least one exhausting opening disposed on the hollow plunger and positioned distant from the first telescoping part.

7. The safety injector of claim 1, further comprising at least one stopper disposed on an outer wall of the hollow plunger and positioned distant from the first telescoping part.

8. The safety injector of claim 1, wherein the raised portion is formed integrally on the outside wall of the retractable plunger and is selected from the group consisting of a plurality of protruding dots and a plurality of adjacent rows of transversely convex annular ribs.

9. The safety injector of claim 1, wherein the depression is selected from the group consisting of a cavity, a groove, a plurality of cavities, and a plurality of adjacent rows of transversely concave annular grooves.

10. A safety injector, comprising:
a needle hub connecting a needle, the needle hub comprising a inserting part therein and a hollow track connecting with the inserting part, the inserting part being for accommodating the needle and the hollow tract further comprising a distal end and a proximal end, the distal end of the hollow tract having a first inner diameter and the proximal end having a second diameter, and the first inner diameter being larger than the second inner diameter, wherein the needle hub further comprises a plurality of slots, slopes, turning chutes and guiding chutes connected serially;
a hollow barrel connecting the needle hub for guiding the needle hub to be drawn back to the hollow barrel after an injection is completed, wherein the hollow barrel comprises a plurality of hooks, the plurality of hooks engaging with the slots to clamp the needle hub; and
a collapsable plunger combination settled in the hollow barrel, the collapsable plunger combination comprising a rod, a hollow plunger and retractable plunger, the rod extending from one end of hollow plunger and toward the needle hub, the hollow plunger comprising a first telescoping part and the retractable plunger comprising a second telescoping part, the first telescoping part telescoping with the second telescoping part, at least one raised portion being disposed on an outside wall of the second telescoping part to be correspondingly embedded in at least one depression disposed on an inside wall of the first telescoping part, the raised portion and the depression engaging to each other;
wherein the engagement between the raised portion and the depression is released to make the retractable plunger retract into the hollow plunger when a following press on the retractable plunger after an injection is completed, and thereby spare a space of the hollow barrel for accommodating the needle hub, and when the following press is applied on the retractable plunger after the injection is completed, the hooks of the hollow barrel disengage with the slots and slide along the slopes, the turning chutes, and the guiding chutes, so that the needle hub is guided and retracted into the hollow barrel.

11. The safety injector of claim 10, further comprising at least one stress adjustable notch disposed on first telescoping part.

12. The safety injector of claim 10, further comprising at least one stress adjustable notch disposed on second telescoping part.

13. The safety injector of claim 10, wherein the bottom of the needle hub further comprises an incline configuration.

14. The safety injector of claim 10, further comprising a protrusion disposed on an inner wall of the hollow barrel and being distant from the needle.

15. The safety injector of claim 10, further comprising at least one exhausting opening disposed on the hollow plunger and positioned distant from the first telescoping part.

16. The safety injector of claim 10, further comprising at a wing disposed on a proximal end of the hollow barrel.

17. The safety injector of claim 10, wherein the raised portion is formed integrally on the outside wall of the retractable plunger and is selected from the group consisting of a plurality of protruding dots and a plurality of adjacent rows of transversely convex annular ribs.

18. The safety injector of claim 10, wherein the depression is selected from the group consisting of a cavity, a groove, a plurality of cavities, and a plurality of adjacent rows of transversely concave annular grooves.

* * * * *